United States Patent [19]
Bernstein et al.

[11] Patent Number: 5,912,015
[45] Date of Patent: Jun. 15, 1999

[54] MODULATED RELEASE FROM BIOCOMPATIBLE POLYMERS

[75] Inventors: Howard Bernstein, Cambridge, Mass.; Yan Zhang, Belmont, Calif.; M. Amin Khan, Carmel, Ind.; Mark A. Tracy, Arlington, Mass.

[73] Assignee: Alkermes Controlled Therapeutics, Inc., Cambridge, Mass.

[21] Appl. No.: 09/056,566

[22] Filed: Apr. 7, 1998

Related U.S. Application Data

[63] Continuation of application No. 08/727,531, filed as application No. PCT/US95/05511, May 3, 1995, abandoned, which is a continuation-in-part of application No. 08/237,057, May 3, 1994, Pat. No. 5,656,297, which is a continuation-in-part of application No. 07/849,754, Mar. 12, 1992, abandoned.

[51] Int. Cl.$^6$ .............................. A61K 9/14; A61K 9/16
[52] U.S. Cl. ..................... 424/484; 424/486; 424/487; 424/489; 514/772.3; 514/772.6; 514/805; 514/965
[58] Field of Search ..................... 424/484, 486, 424/487, 488, 489; 514/772.3, 772.6, 965

[56] References Cited

U.S. PATENT DOCUMENTS

| | | | |
|---|---|---|---|
| 3,523,906 | 8/1970 | Vrancken et al. | 252/316 |
| 3,691,090 | 9/1972 | Kitajima et al. | 252/316 |
| 3,737,337 | 6/1973 | Schnoring et al. | 117/100 |
| 3,887,699 | 6/1975 | Yolles | 424/19 |
| 3,891,570 | 6/1975 | Fukushima et al. | 252/316 |
| 3,928,566 | 12/1975 | Briggs et al. | 424/94 |
| 4,166,800 | 9/1979 | Fong | 252/316 |
| 4,235,236 | 11/1980 | Theeuwes | 128/260 |
| 4,237,114 | 12/1980 | Cardarelli | 424/78 |
| 4,252,791 | 2/1981 | Grossberg et al. | 424/85 |
| 4,389,330 | 6/1983 | Tice et al. | 427/213.36 |
| 4,391,797 | 7/1983 | Folkman et al. | 424/19 |
| 4,530,840 | 7/1985 | Tice et al. | 514/179 |

(List continued on next page.)

FOREIGN PATENT DOCUMENTS

| | | |
|---|---|---|
| 0 123 291 A2 | 10/1984 | European Pat. Off. . |
| 0 251 680 A2 | 1/1988 | European Pat. Off. . |
| 0266119 A3 | 5/1988 | European Pat. Off. . |
| 0 281 299 A1 | 9/1988 | European Pat. Off. . |
| 0 307 097 A2 | 3/1989 | European Pat. Off. . |

(List continued on next page.)

OTHER PUBLICATIONS

Pratt, L., et al., "The Effect of Ionic Electrolytes on Hydrolytic Degradation of Biodegradable Polymers: Mechanical and Thermodynamic Properties and molecular Modeling," *J. Polymer Science* 31(7):1759–1769 (1993).

(List continued on next page.)

*Primary Examiner*—Thurman K. Page
*Assistant Examiner*—James M. Spear
*Attorney, Agent, or Firm*—Hamilton, Brook, Smith & Reynolds, P.C.

[57] ABSTRACT

The present invention relates to a composition for the modulated release of a biologically active agent. The composition comprises a biocompatible polymeric matrix, a biologically active agent which is dispersed within the polymeric matrix, and a metal cation component which is separately dispersed within the polymeric matrix, whereby the metal cation component modulates the release of the biologically active agent from the polymeric matrix. The present invention also relates to a method for modulating the release of a biologically active agent from a biocompatible polymeric matrix, comprising the steps of dissolving a biocompatible polymer in a solvent to form a polymer solution and also separately dispersing a metal cation component and a biologically active agent within the polymer solution. The polymer solution is then solidified to form a polymeric matrix, wherein at least a significant portion of the metal cation component is dispersed in the polymeric matrix separately from the biologically active protein, and whereby the metal cation component modulates the release of the biologically active agent from the polymeric matrix.

8 Claims, 14 Drawing Sheets

U.S. PATENT DOCUMENTS

| | | | |
|---|---|---|---|
| 4,530,901 | 7/1985 | Weissmann | 435/70 |
| 4,542,025 | 9/1985 | Tice et al. | 424/78 |
| 4,637,905 | 1/1987 | Gardner | 264/4.3 |
| 4,655,777 | 4/1987 | Dunn et al. | 623/16 |
| 4,675,189 | 6/1987 | Kent et al. | 424/490 |
| 4,711,782 | 12/1987 | Okada et al. | 424/455 |
| 4,732,889 | 3/1988 | Cynshi et al. | 514/8 |
| 4,767,628 | 8/1988 | Hutchinson | 424/426 |
| 4,806,524 | 2/1989 | Kawaguchi et al. | 514/8 |
| 4,835,139 | 5/1989 | Tice et al. | 514/15 |
| 4,853,218 | 8/1989 | Yim et al. | 424/85.7 |
| 4,871,538 | 10/1989 | Yim et al. | 424/85.7 |
| 4,879,272 | 11/1989 | Shimoda et al. | 514/8 |
| 4,891,225 | 1/1990 | Langer et al. | 424/428 |
| 4,897,268 | 1/1990 | Tice et al. | 424/422 |
| 4,906,474 | 3/1990 | Langer et al. | 424/428 |
| 4,962,091 | 10/1990 | Eppstein et al. | 514/2 |
| 4,981,696 | 1/1991 | Loomis et al. | 424/486 |
| 4,992,419 | 2/1991 | Woog et al. | 514/8 |
| 5,019,400 | 5/1991 | Gombotz et al. | 424/497 |
| 5,075,115 | 12/1991 | Brine | 424/486 |
| 5,122,367 | 6/1992 | Ron et al. | 424/80 |
| 5,126,147 | 6/1992 | Silvestri et al. | 424/497 |
| 5,145,674 | 9/1992 | Lane et al. | 424/78.08 |
| 5,176,907 | 1/1993 | Leong | 424/78.08 |
| 5,192,741 | 3/1993 | Orsolini et al. | 514/4 |
| 5,344,654 | 9/1994 | Rueger et al. | 424/423 |
| 5,413,797 | 5/1995 | Khan et al. | 424/489 |
| 5,441,734 | 8/1995 | Reichert et al. | 424/85.7 |
| B1 4,985,404 | 4/1992 | Mitchell | 514/6 |

FOREIGN PATENT DOCUMENTS

| | | |
|---|---|---|
| 0330180 A1 | 8/1989 | European Pat. Off. . |
| 0537559 A1 | 4/1993 | European Pat. Off. . |
| 0580 428 A1 | 1/1994 | European Pat. Off. . |
| 0633 020 A1 | 1/1995 | European Pat. Off. . |
| 89/03678 | 5/1989 | WIPO . |
| 90/09166 | 8/1990 | WIPO . |
| 90/13285 | 11/1990 | WIPO . |
| 90/13780 | 11/1990 | WIPO . |
| 0 595 030 A2 | 9/1991 | WIPO . |
| 91/12882 | 9/1991 | WIPO . |
| 91/18927 A1 | 12/1991 | WIPO . |
| 92/11844 | 7/1992 | WIPO . |
| 92/19226 | 11/1992 | WIPO . |
| 93/02712 | 2/1993 | WIPO . |
| 93/07861 | 4/1993 | WIPO . |
| 93/17668 | 9/1993 | WIPO . |
| 93/25221 | 12/1993 | WIPO . |
| 94/19373 A1 | 1/1994 | WIPO . |
| 94/07469 | 4/1994 | WIPO . |
| 94/12158 | 9/1994 | WIPO . |
| 95/11010 | 4/1995 | WIPO . |
| 95/29664 A1 | 9/1995 | WIPO . |
| 96/07399A1 | 3/1996 | WIPO . |

OTHER PUBLICATIONS

Costantino, H. R., et al., "Solid–Phase Aggregation of Proteins under Pharmaceutically Relevant Conditions," *J. of Pharmaceutical Sciences*, 83(12):1662–1669 (1994).

Costantino, H. R., et al., "Moisture–Induced Aggregation of Lyophilized Insulin," *Pharmaceutical Research*, 11(1):21–29 (1994).

Costantino, H.R., et al., "Aggregation of a Lyophilized Pharmaceutical Protein, Recombinant Human Albumin: Effect of Moisture and Stabilization by Excipients," *Biotechnology*, 13:493–496 (1995).

Creighton, T.E., "Physical Forces That Determine the Properties of Proteins," *In Proteins, Structures and Molecular Principles*, (NY: W.H. Freeman and Company), pp. 149–150.

Cunningham, B. C., et al., "Dimerization of Human Growth Hormone by Zinc," *Science*, 253:545–548 (Aug. 1991).

Sato, Toyomi, et al., "Porous Biodegradable Microspheres for Controlled Drug Delivery. I. Assessment of Processing Conditions and Solvent Removal Techniques," *Pharmaceutical Research*, 5(1):21–29 (1988).

Langer, R., "New Methods of Drug Delivery," *Science*, 249:1527–1533 (Sep. 1990).

Liu, W. R., et al., "Moisture–Induced Aggregation of Lyophilized Proteins in the Solid State," *Biotechnology and Bioengineering*, 37:177–184 (1991).

Lu, W., and park, T. G., "Protein Release from poly(lactic- –co–glycolic acid) Microspheres: Protein Stability Problems," *PDA J. of Pharmaceutical Science & Technology*, 49(1):13–19 (Jan.–Feb. 1995).

Cohen, S., et al., "Controlled Delivery Systems for Proteins Based on Poly(Lactic/Glycolic Acid) Microspheres," *Pharmaceutical Research*, 8(6):713–720 (1991).

Hora, M.S. et al., "Release of Human Serum Albumin from Poly(lactide–co–glycolide) Microspheres," *Pharmaceutical Research*, 7(11):1190–1194 (1990).

Hageman, M.J., et al., "Preformulation Studies Oriented Toward Sustained Delivery of Recombinant Somatotropins," *J. Agric. Food Chem.*, 40:348–355 (1992).

Cleland, J. L., et al., "Characterization of Recombinant Human Growth Hormone–PLGA Formulations in Animals," *Proceed, Intern. Symp. Control. Rel. Bioact. Mater.*, 22:143–144 (1995).

Cleland, J. L., et al., "One Month Continuous Release Recombinant Human Growth Hormone–PLGA Formulations," *Proceed. Intern. Symp. Control. Rel. Bioact. Mater.*, 22:149–150 (1995).

Mullerad, J., et al., "Delivery of IL–1 Microspheres to Tumor Macrophages," *Proceed. Intern. Symp. Control. Rel. Bioact. Mater.*, 22:512–513 (1995).

Cleland, J. L., et al., "In Vitro Release of Bioactive Recombinant Human Interferon–γ From PLGA Microspheres," *Proceed. Intern. Symp. Control. Rel. Bioact. Mater.*, 22:518–519 (1995).

Park, T. G., et al., "Importance of In Vitro Experimental Conditions on Protein Release Kinetics, Stability and Polymer Degradation in Protein Encapsulated Poly(D,:–Lactic Acid–Co–Glycolic Acid) Microspheres," *J. of Controlled Release*, 33:211–222 (1995)

Nagata, S., et al., "Synthesis in *E. Coli* of a Polypeptide with Human Leukocyte Interferon Activity," *Nature*, 284:316–320 (Mar. 1980).

Rubinstein, M., "The Structure of Human Interferons," *Biochimica et Biophysica Acta.*, 695:5–16 (1982).

Sah, H., et al., "The Influence of Biodegradable Microcapsule Formulations on the Controlled Release of a Protein," *J. of Controlled Release* 30:201–211 (1994).

MODULATED RELEASE FROM BIOCOMPATIBLE POLYMERS

RELATED APPLICATIONS

This application is a continuation of U.S. patent application Ser. No. 08/727,531, filed on Oct. 22, 1996, now abandoned, which is the U.S. National Phase of International application PCT/US95/05511 filed May 3, 1995, which is a continuation-in-Part of U.S. patent application Ser. No. 08/237,057 filed on May 3, 1994, now U.S. Pat. No. 5,656,297, which is a continuation-in-part of U.S. Ser. No. 07/849,754, now abandoned. Each of the above documents are incorporated by reference in their entirety.

BACKGROUND OF THE INVENTION

Many illnesses or conditions require a constant level of medicaments or agents in vivo to provide the most effective prophylactic, therapeutic or diagnostic results. In the past, medicaments were given in doses at intervals which resulted in fluctuating medication levels.

Attempts to control and steady medication levels have more recently included the use of many biodegradable substances, such as poly(lactide) or poly(lactide-co-glycolide) microspheres containing the medicament. The use of these microspheres provided an improvement in the controlled release of medicaments by utilizing the inherent biodegradability of the polymer to improve the release of the medicament and provide a more even, controlled level of medication. However, in some cases, biodegradable polymers under in vivo conditions can have an initial level of medicament release, which is too high or too low, and after a period of hydration can substantially degrade to thereby limit the effective life of the controlled release microspheres. Therefore, a need exists for a means of modulating the controlled release of medicament from a biodegradable polymer to provide a higher level of initial medicament release and to provide longer periods of fairly consistent medicament release levels in vivo.

SUMMARY OF THE INVENTION

The present invention relates to a composition for the modulated release of a biologically active agent. The composition comprises a biocompatible polymeric matrix, a biologically active agent which is dispersed within the polymeric matrix, and a metal cation component which is separately dispersed within the polymeric matrix, whereby the metal cation component modulates the release of the biologically active agent from the polymeric matrix.

The present invention also relates to a method for modulating the release of a biologically active agent from a polymeric matrix, comprising the steps of dissolving a biocompatible polymer in a solvent to form a polymer solution and also separately dispersing a metal cation component and a biologically active agent within said polymer solution. The polymer solution is then solidified to form a polymeric matrix, wherein at least a significant portion of the metal cation component is dispersed in the polymeric matrix separately from the biologically active protein, and whereby the metal cation component modulates the release of the biologically active agent from the polymeric matrix.

This invention has the advantage of modulating the release of a biologically active agent in vivo from a biodegradable polymer, thereby enhancing the control of the level of prophylactic, therapeutic and diagnostic agents released in vivo and lengthening the period during which controlled release can be maintained for a single dose.

DETAILED DESCRIPTION OF THE INVENTION

Figure 1:
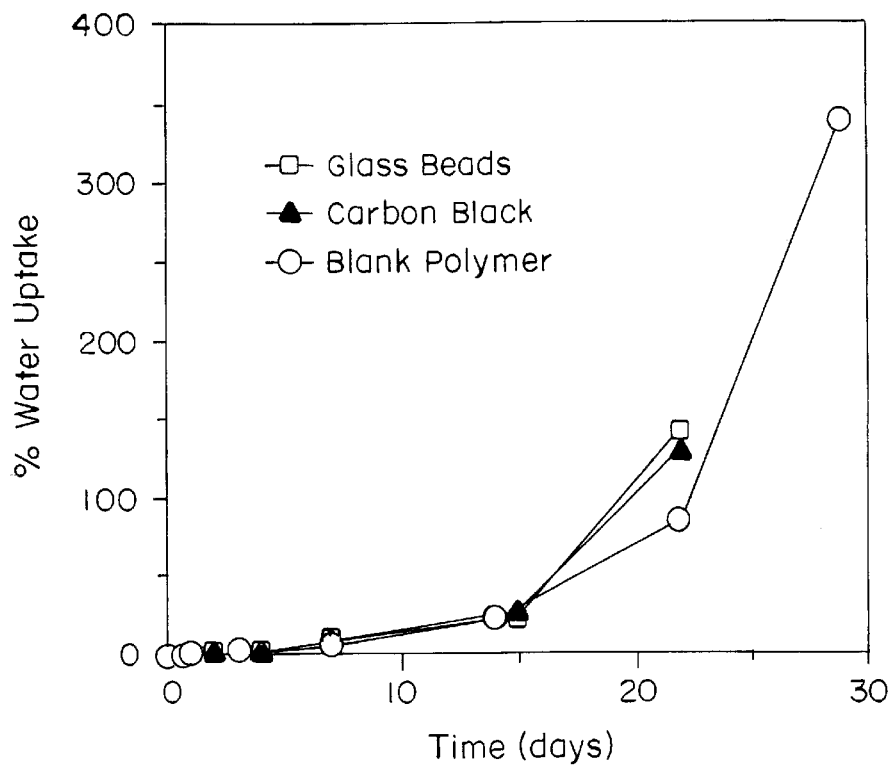
FIG. 1 is a plot of percent water uptake (% w/w) as a function of time in 10 mM HEPES for the following polymer films: a) blank poly(lactide-co-glycolide) (hereinafter "PLGA"), b) PLGA containing glass beads, and c) PLGA containing carbon black, illustrating the effect of glass beads and carbon black on PLGA film water absorption.

A modulated release of a biologically active agent, as defined herein, is a release of a biologically active agent from a biocompatible polymeric matrix containing a dispersed metal cation component which is separate from the biologically active agent. In a modulated release, at least one release characteristic, such as initial release level of said agent, subsequent agent release levels, the amount of agent released, and/or the extent of the release period, is changed from the release characteristic(s) demonstrated for said biologically active agent from a polymeric matrix not containing a dispersed metal cation component by the selection of the type and amount of metal cation component dispersed in the polymeric matrix.

A polymer of the polymeric matrix of this composition is a biocompatible polymer which can be either a biodegradable or non-biodegradable polymer, or blends or copolymers thereof.

Biodegradable, as defined herein, means the composition will degrade or erode in vivo to form smaller chemical species. Degradation can result, for example, by enzymatic, chemical, and physical processes. Suitable biocompatible, biodegradable polymers include, for example, poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, blends and copolymers thereof.

Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

A polymer, or polymeric matrix, is biocompatible if the polymer, and any degradation products of the polymer, are non-toxic to the recipient and also present no significant deleterious or untoward effects on the recipient's body.

Further, the polymer can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl radical. An unblocked polymer is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 5,000 Daltons to about 42,000 Daltons A biologically active agent, as defined herein, is an agent which possesses therapeutic, prophylactic or diagnostic properties in vivo. Examples of suitable therapeutic and/or prophylactic biologically active agents include proteins, such as hormones, antigens, growth factors, etc.; nucleic acids, such as antisense molecules; and small molecules, such as antibiotics, steroids, decongestants, neuroactive agents, anesthetics and sedatives. Examples of suitable diagnostic and/or therapeutic biologically active agents include radioactive isotopes and radiopaque agents.

In the modulated release composition of the present invention, an effective amount of particles of a biologically active agent is dispersed within a polymeric matrix. An effective amount of a biologically active agent is a therapeutically, prophylactically or diagnostically effective amount, which can be determined by a person of ordinary skill in the art taking into consideration factors such as body weight; age; physical condition; therapeutic, prophylactic or diagnostic goal desired, type of agent used, type of polymer used, initial burst and subsequent release levels desired, and release rate desired. Typically, a polymeric matrix for modulating the release of a biologically active agent will contain from about 0.011 (w/w) biologically active agent to about 50% (w/w) biologically active agent, by weight.

Particles of a biologically active agent include, for example, crystalline particles, non-crystalline particles, freeze dried particles, and lyophilized particles. The particles may contain only the biologically active agent or may also contain a stabilizing agent and/or other excipient.

In one embodiment, a biologically active agent is a protein. Preferred proteins for inclusion in a modulated release composition include, for example, nucleases, erythropoietin, human growth hormone, interferons, interleukins, tumor necrosis factor, adrenocorticotropic hormone, growth factors, and colony-stimulating factors.

A modulated controlled release composition may also contain more than one biologically active agent, for instance, two different proteins, such as erythropoietin and granulocyte-macrophage colony-stimulating factor.

A metal cation component, as defined herein, is a component containing at least one kind of multivalent metal cation (having a valence of +2 or more) in a non-dissociated state, a dissociated state, or a combination of non-dissociated and dissociated states. Suitable metal cation components include, for instance, metal salts, metal hydroxides, and basic (pH of about 7 or higher) salts of weak acids wherein the salt contains a metal cation. It is preferred that the metal cation be divalent.

In the modulated release composition of the present invention, a suitable concentration of a metal cation component is dispersed within a polymer matrix. A suitable concentration of a metal cation component is any concentration of a metal cation component which will modulate the release of a biologically active agent from a polymeric matrix. In one embodiment, suitable proportions of a metal cation component to be dispersed in a polymer are between about 1% (w/w) to about 30% (w/w). The optimum ratio depends upon the polymer, the metal cation component, and the biologically active agent utilized. In a preferred embodiment, suitable amounts of a metal cation component to be dispersed in a polymer are between about 5% (w/w) to about 20% (w/w).

In one embodiment, the metal cation component is substantially insoluble in aqueous fluids. Substantial insolubility in aqueous fluids, as defined herein, means that the metal cation component is generally not soluble, or is of low solubility, in water or fluids, such as PBS, HEPES or alimentary track fluids. Examples of suitable insoluble metal cation components include, or contain, for instance, $Mg(OH)_2$, magnesium carbonate (such as $4MgCO_3 \cdot Mg(OH)_2 \cdot 5H_2O$), zinc carbonate (such as $3Zn(OH)_2 \cdot 2ZnCO_3$), $CaCO_3$, $Zn_3(C_6H_5O_7)_2$ (hereinafter zinc citrate) or combinations thereof.

In an alternate embodiment, the metal cation component is substantially soluble in aqueous fluids. Substantial solubility in aqueous fluids, as defined herein, means that the metal cation component is generally soluble in water or fluids, such as PBS, HEPES or alimentary track fluids. Suitable soluble metal cation components include, or can contain, for example, $Mg(OAc)_2$, $MgSO_4$, $Zn(OAc)_2$, $ZnSO_4$, $ZnCl_2$, $MgCl_2$, $Mg_3(C_6H_5O_7)_2$ (hereinafter magnesium citrate), and combinations thereof.

In yet another embodiment, the metal cation component is a combination of substantially soluble and insoluble components.

In one embodiment of the method for modulating the release of a biologically active agent from a polymeric matrix, a suitable polymer is dissolved in a solvent to form a polymer solution. Examples of suitable solvents include, for instance, polar organic solvents such as methylene chloride, chloroform, tetrahydrofuran, dimethyl sulfoxide, and hexafluoroisopropanol.

Particles of at least one metal cation component are then dispersed within the polymer solution. Suitable means of dispersing a metal cation component within a polymer solution include sonication, agitation, mixing, and homogenization. It is understood that a metal cation component can be added directly to the polymer solution as a solid, preferentially in particulate form, wherein the metal cation component will either then be suspended as solid particles dispersed within the polymer solution, or the metal cation component will then dissociate within the polymer solution to form free metal cations. It is also understood that, before addition to a polymer solution, a metal cation component can be suspended as solid particles or dissolved in a second solvent, wherein the second solvent is then added to the polymer solution. A second solvent is suitable if it is the same solvent as the polymer's solvent, or if the second solvent is miscible with the polymer's solvent and the polymer is soluble in the second solvent. An example of a suitable second solvent is acetone.

In another embodiment, a metal cation component can be suspended or dissolved in a solvent, after which a suitable polymer is then dissolved in said solvent.

At least one biologically active agent is also added to the polymer solution separately from the addition of the metal cation component, metal cation component suspension, or metal cation component solution. In one embodiment, the biologically active agent is dissolved in a solvent, which is also suitable for the polymer, and then mixed into the polymer solution.

It is to be understood that a metal cation component and a biologically active agent can be added to the polymer solution sequentially, in reverse order, intermittently or through separate, concurrent additions. It is also understood that a biologically active agent can be suspended in a solution, or suspension, of a metal cation component in a solvent before dissolving the polymer in said solvent.

The amount of a biologically active agent added to the polymer solution can be determined empirically by comparative in vitro tests of polymeric matrices containing different concentrations of at least one metal cation component and of at least one biologically active agent. The amount used will vary depending upon the particular agent, the desired effect of the agent at the planned release levels, and the time span over which the agent will be released.

The formation of a polymeric matrix microparticles for modulating the release of RNase-A, ACTH, Interferon-α,2b and human growth hormone (hGH) is further described in Examples IX, X, XI and XII. The effectiveness of the method of modulating the in vitro release of RNase-A or ACTH from polymeric microspheres is also described in Example IX. Further, the effectiveness of the method of modulating the in vivo release of Interferon-α,2b from a polymeric microspheres is described in Example X. Additionally, the effectiveness of the method of modulating the in vivo release of hGH from a polymeric microspheres is demonstrated by Examples XI and XII.

In an alternate embodiment, the protein added to the polymer solution can be mixed with an excipient, such as at least one stabilizing agent as is known in the art.

The polymeric matrix of this invention can be formed into many shapes such as a film, a pellet, a cylinder, a disc, or a microparticle. A microparticle, as defined herein, comprises a particle having a diameter of less than about one millimeter containing particles of a biologically active agent dispersed therein. A microparticle can have a spherical, non-spherical, or irregular shape. The preferred microparticle shape is a sphere.

In a preferred embodiment, the method includes forming a modulated release polymeric matrix as a microparticle. A suitable metal cation component is dispersed as solid particles or free dissociated cations, and a biologically active agent is separately dispersed as solid particles in a polymer solution containing about 5–30% polymer by weight. In a more preferred embodiment, the polymer solution contains about 5–15% polymer by weight. Biodegradable polymers are preferred, while PLGA is more preferred.

A microparticle is then formed from the polymer solution. A suitable method for forming an acceptable microsphere from a polymer solution is described in U.S. Pat. No. 5,019,400, issued to Gombotz et al. The teachings of U.S. Pat. No. 5,019,400 are incorporated herein by reference.

In another embodiment, a modulated release composition is prepared by the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al., which are incorporated herein by reference.

In the solvent evaporation method a polymer solution, which contains a dispersed metal cation component and a dispersed biologically active agent, is mixed in or agitated with a continuous phase, in which the polymer's solvent is substantially immiscible, to form an emulsion. The continuous phase is usually an aqueous solvent. Emulsifiers are often included in the continuous phase to stabilize the emulsion. The polymer's solvent is then evaporated over a period of several hours or more, thereby solidifying the polymer to form a polymeric matrix having a metal cation component and a biologically active agent separately dispersed therein.

In another embodiment, the method includes forming a modulated release polymeric matrix as a film or any other shape. A polymer solution and metal cation component, in particulate or dissociated form, are mixed, for instance by sonication, until the metal cations are generally dispersed throughout the polymer solution. The polymer solution is subsequently cast in a mold, such as a petri dish. The solvent is then removed by means known in the art until a film or form, with a constant dry weight, is obtained. The formation of polymeric matrix films and polymer pellets is further described in Examples I and II.

Several other methods of using the composition of this invention can be used to modulate physical properties of polymers. One embodiment of the method of use consists of a method for modifying the water absorption, or hydration capacity without significant polymer degradation. The method comprises forming a solution of a polymer and then dispersing a metal cation component into the polymer solution. The polymer solution is then solidified to form a polymer matrix wherein the metal cation component is dispersed therein. See Example III for a further description of this method of enhancing initial hydration.

A further embodiment of the method of use consists of a method for significantly stabilizing the glass transition temperature for a polymer during hydration, comprising the steps of forming a solution of a polymer and a solvent and then dispersing a metal cation component within said polymer solution. The polymer solution is then solidified to form a polymer matrix wherein particles of the metal cation component are dispersed therein.

Glass transition temperature (Tg) could be an indirect indicator of polymeric degradation since Tg is a function of the molecular weight of the polymer and usually decreases as molecular weight decreases. Glass transition temperature (Tg) is defined as the temperature at which a polymer converts from a glass phase to a rubbery phase. Tg is affected by the molecular weight of the polymer. See Example V for further description of this method of stabilizing Tg during polymer hydration. In the embodiment wherein the polymeric matrix is in the form of microparticles, the stabilization of Tg maintains the mechanical properties of the polymer, thereby enhancing the control of agent release.

Yet another embodiment of the method of use consists of a method for increasing the porosity of a polymer without significant polymer degradation. This method includes the steps of forming a solution of a polymer and a solvent and then dispersing a metal cation component into said polymer solution. The polymer solution is then solidified to form a polymer matrix wherein the metal cation compound is dispersed therein and subsequently hydrated to form at least one gap within said polymeric matrix, thereby increasing the porosity of the polymer. Gaps, as defined herein, comprise pores and/or voids. See Example VI for a further description of this method of use.

An alternate embodiment of the method of use consists of a method for slowing the rate of degradation of a polymer. In this method a solution is formed of a polymer, and a metal cation component is then dispersed within said polymer solution. The polymer solution is subsequently solidified to form a polymeric matrix having a metal cation component dispersed therein. Examples IV, VII, and VIII provide additional descriptions of the modulating polymeric degradation rate, both in vitro and in vivo, as the result of the addition of metal cations to the polymer and from the selection of polymer end groups.

The composition of this invention can be administered to a human, or other animal, for example, by injection and/or implantation subcutaneously, intramuscularly, intraperitoneally, intradermally, intravenously, intraarterially, or intrathecally; by administration to mucosal membranes, such as intranasally or by means of a suppository, or by in situ delivery to provide the desired dosage of a biologically active agent based on the known parameters for treatment of the various medical conditions with said agent.

The invention will now be further and specifically described by the following examples.

EXEMPLIFICATIONS

EXAMPLE I

PREPARATION OF POLYMER FILMS CONTAINING SALTS

Blocked-PLGA (50:50) with a molecular weight of 42,000 Daltons (I.V. 0.7 dl/g Birmingham Polymers, Birmingham Ala.) was used for all film studies. The polymer films were produced by a film casting technique. The polymer was dissolved in methylene chloride (5% w/v) at room temperature for up to 24 hours.

Films were prepared using both water insoluble and soluble salts containing divalent cations. The salts were incorporated in the polymer either as particulates or by cosolubilizing the salts with the polymer in an appropriate cosolvent. The fabrication procedure is described below.

Three salts with low water solubility, $MgCO_3$, $Mg(OH)_2$ and $ZnCO_3$ (Spectrum Chemical MFG, Corp., Gardena, Calif.), and two water soluble salts, $MgSO_4$ and $ZnSO_4$ (Spectrum Chemical MFG, Corp., Gardena, Calif.), were incorporated into films as particulates. $MgCO_3$, $Mg(OH)_2$, and $ZnCO_3$ were sieved prior to film casting using a 38 micron U.S.A. standard testing sieve to control the particle size. The average particle diameter of the sieved salts prior to encapsulation is provided in Table 1.

TABLE 1

| Salt | Formula | Diameter ($\mu$m) |
|---|---|---|
| $MgCO_3$ | $4MgCO_3 \cdot Mg(OH)_2 \cdot 5H_2O$ | 2.5 |
| $Mg(OH)_2$ | $Mg(OH)_2$ | 2.5 |
| $ZnCO_3$ | $3Zn(OH)_2 \cdot 2ZnCO_3$ | 4.0 |

As non-ionic water insoluble particulates, either carbon black or glass particles (20 micron diameter, Polysciences Inc., Warrington, Pa.) were used. Polymer films were prepared by adding the sieved salt to the polymer solution to a final concentration in the 0–30% (w/w, salt/polymer) range. The salt polymer suspension was sonicated for approximately four minutes to disperse the salt particles. A sample of 100 ml of the suspension was then cast in 9×5×1 inch Teflon petri dish (Plastic Structures Co., Wilmington, Mass.). The control polymer film was the polymer containing 0.0% salt.

The films were cast in two layers to avoid settling of the salt particles. The methylene chloride was evaporated at room temperature in a hood for the first 24 hours at atmospheric pressure. The films were transferred to a vacuum oven and were dried at 30° C. for 6 hours, 40° C. for 3 days, and then at 50° C. for 3 days. No further reduction in dry weight was observed at the end of this drying cycle.

Polymer films containing the water soluble salts, magnesium acetate and zinc acetate, were prepared by cosolubilizing the salts with PLGA in acetone. A 10% solution of polymer was prepared by dissolving 5 g of polymer in 50 ml of acetone at room temperature. A solution of $Mg(OAc)_2$ or $Zn(OAc)_2$ was prepared by dissolving 0.26 g of either salt in 50 ml of room temperature acetone. Equal volumes of the salt solution and the polymer solution were combined, and the mixture was sonicated for approximately four minutes. One hundred milliliter samples of the salt-polymer solution were poured into the Teflon petri dishes. The methylene chloride was evaporated as described previously.

EXAMPLE II

PREPARATION OF POLYMER PELLETS CONTAINING SALTS

Blocked and unblocked-PLGA (50:50) polymers (respectively, RG502 (Mw 12,700 Daltons) and RG502H (Mw 9,300 Daltons); Boehringer Ingelheim Chemicals, Inc., Montvale, N.J.) were used for all polymer pellet studies. Samples of the blocked-PLGA and unblocked-PLGA were mixed with $MgCO_3$ (10% w/w) or $ZnCO_3$ (10% w/w) and were incorporated into the pellets as particulates. Prior to mixing into the PLGA, the salts were sieved as described in Example I to control the particle size. Blocked-PLGA and unblocked-PLGA polymer pellets containing 0.0% salt were used as controls.

The polymer pellets of blocked-PLGA or unblocked-PLGA, (containing 0.0% salt, 10% w/w $MgCO_3$ or 10% w/w $ZnCO_3$) were prepared using a Carver Laboratory Press Model C. Each polymer sample was heated at 60° C. for 10 minutes and then pressed for 1 minute at 15,000 pounds to form polymer pellets.

EXAMPLE III

WATER UPTAKE IN POLYMER FILMS AND PELLETS

Water uptake studies were conducted on the polymer films of Example I and the control polymer pellets of Example II. The buffer solutions used in this study were HEPES (10 mM HEPES, 130 mM NaCl, 0.1% $NaN_3$, 0.1% Pluronics F68, pH 7.3) or PBS (50 mM Sodium Phosphate, 78 mM NaCl, 0.1% $NaN_3$, 0.1% Pluronics F68, pH 7.2). Polymer film samples (50–80 mg) were incubated in buffer (0.5 ml/mg film) at 37° C. Polymer pellet samples (160 mg) were incubated in buffer (0.1 ml/mg of pellet) at 37° C. When incubated, the pellets were placed in scintillation vials. Duplicate polymer film samples were utilized for each of the time points to enable both dry and wet weight measurements.

Samples were recovered at the specified time intervals, the surface water removed with absorbent paper, and the samples were weighed. Water uptake (wet weight) of the polymer samples was then determined gravimetrically.

The polymer film and pellet samples were then frozen at −80° C. and subsequently lyophilized for 3–4 days until a constant dry weight was achieved. The weights of the dried films were measured after lyophilization. Buffer solution was replaced in full for the film samples being incubated for the later water uptake determinations.

Water uptake was calculated at each time point using the following equation:

$$\% \text{ H}_2\text{O Uptake} = \frac{\text{Wt. hydrated} - \text{Wt. dried}}{\text{Wt. dried}} \times 100$$

Values obtained for duplicate samples of films were averaged.

The effects of different salts on the water uptake of Values blocked-PLGA films are shown in FIGS. 1–8. The control films (blank films) without incorporated salts showed a slow, gradual increase in the amount of water absorbed during the first 15 to 20 days (FIG. 1). After this time, a large increase in water uptake was observed. This secondary phase of water uptake was associated with polymer degradation (see Example IV). Films containing inert particles (carbon black or glass particles) exhibited water uptake profiles similar to the control polymer films (FIG. 1).

Figure 2:
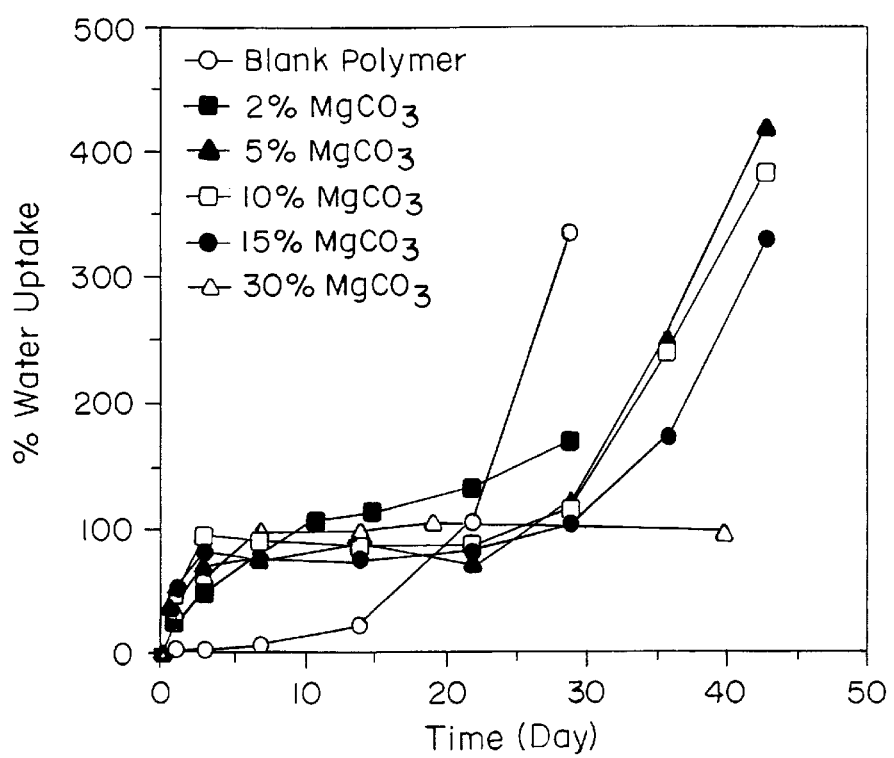
FIG. 2 is a plot of percent water uptake (% w/w) as a function of hydration time in 10 mM HEPES for the following polymer films: a) blank PLGA, b) PLGA containing 2% $MgCO_3$, c) PLGA containing 5% $MgCO_3$, d) PLGA containing 10% $MgCO_3$, e) PLGA containing 15% $MgCO_3$, and f) PLGA containing 30% $MgCO_3$, illustrating the effect of $MgCO_3$ at different concentrations on PLGA film water absorption.
Figure 3:
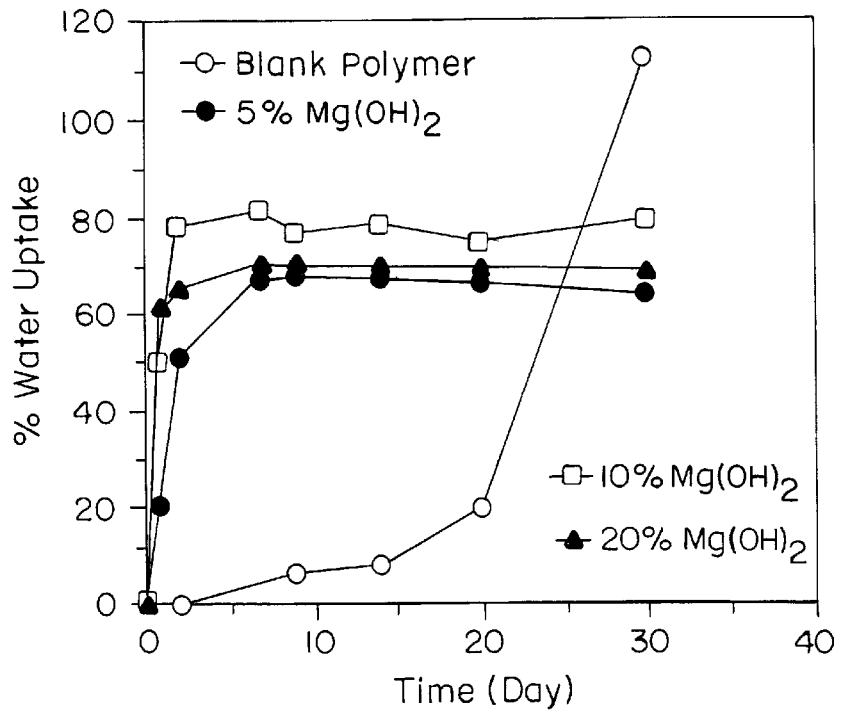
FIG. 3 is a plot of percent water uptake (% w/w) as a function of hydration time in 50 mM PBS for the following polymer films: a) blank PLGA, b) PLGA containing 5% $Mg(OH)_2$, c) PLGA containing 10% $Mg(OH)_2$, and d) PLGA containing 20% $Mg(OH)_2$, illustrating the effect of $Mg(OH)_2$ at different concentrations on PLGA film water absorption.
Figure 4:
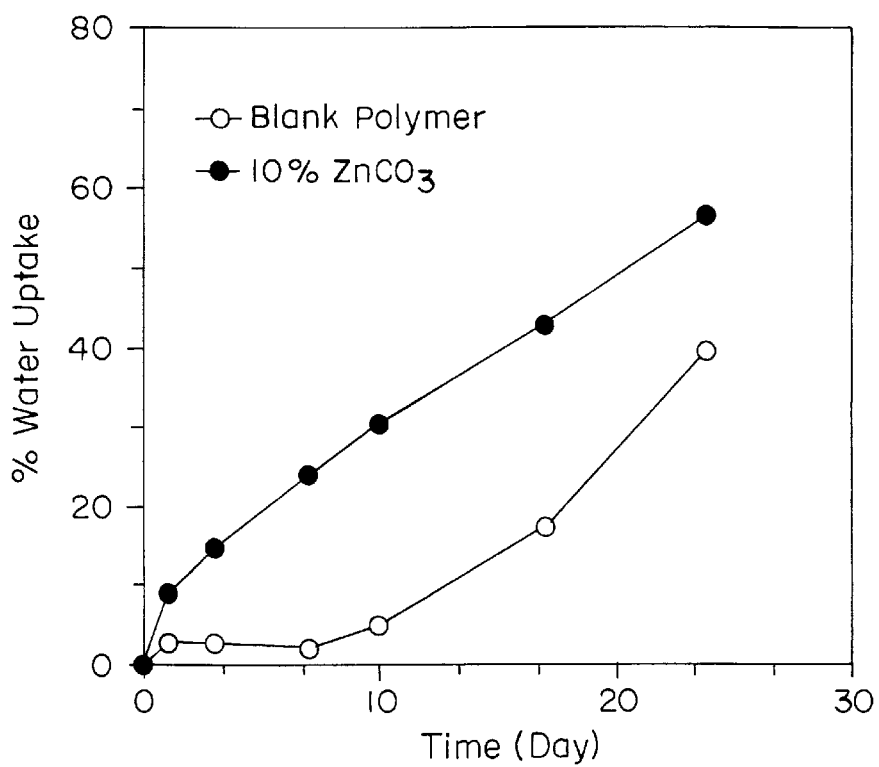
FIG. 4 is a plot of percent water uptake (% w/w) versus hydration time in 50 mM PBS for the following polymer films: a) blank PLGA and b) PLGA, containing 10% $ZnCO_3$, illustrating the effect of $ZnCO_3$ on PLGA film water absorption.
Figure 5:
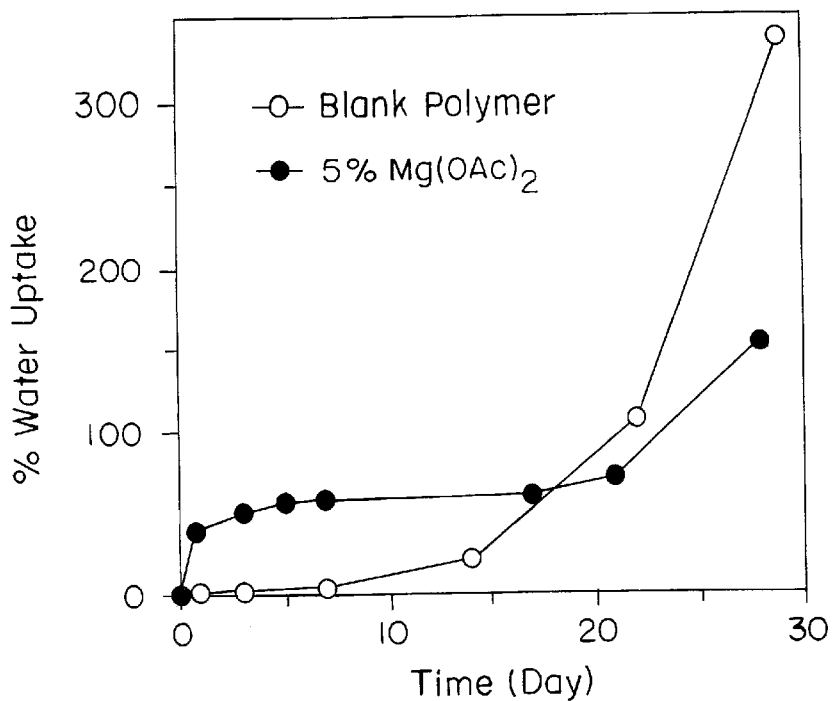
FIG. 5 is a plot of percent water uptake (% w/w) versus hydration time in 10 mM HEPES for the following polymer films: a) blank PLGA and b) PLGA, containing 5% $Mg(OAc)_2$, illustrating the effect of $Mg(OAc)_2$ on PLGA film water absorption.

Films containing insoluble salts ($MgCO_3$, $Mg(OH)_2$ and $ZnCO_3$) all exhibited a greater initial water uptake than control films (FIGS. 2–4). Following the initial uptake phase, about 3 days, the amount of water absorbed by the films containing $MgCO_3$ and $Mg(OH)_2$ did not change until after 30 days. The second phase of water uptake occurred approximately 2 weeks later than was observed with control polymer films.

$ZnCO_3$ films exhibited a more continuous water uptake of a magnitude greater than that of control films (FIG. 4). There was no clear distinction between initial and secondary water uptake phases in the $ZnCO_3$ films.

Figure 6:
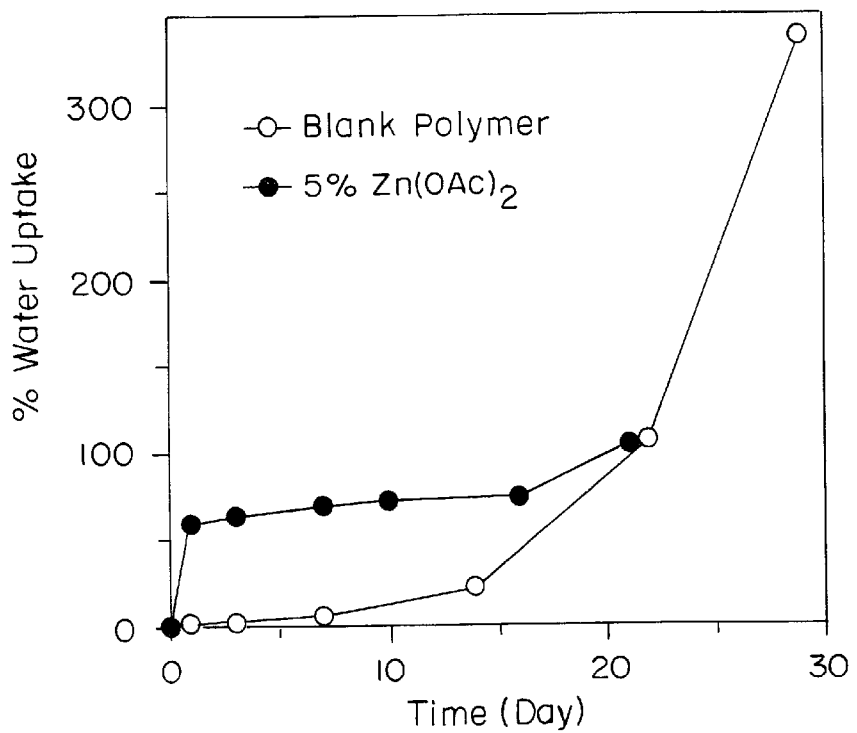
FIG. 6 is a plot of percent water uptake (% w/w) versus hydration time in 10 mM HEPES for the following polymer films: a) blank PLGA and b) PLGA, containing 5% $Zn(OAc)_2$, illustrating the effect of $Zn(OAc)_2$ on PLGA film water absorption.
Figure 7:
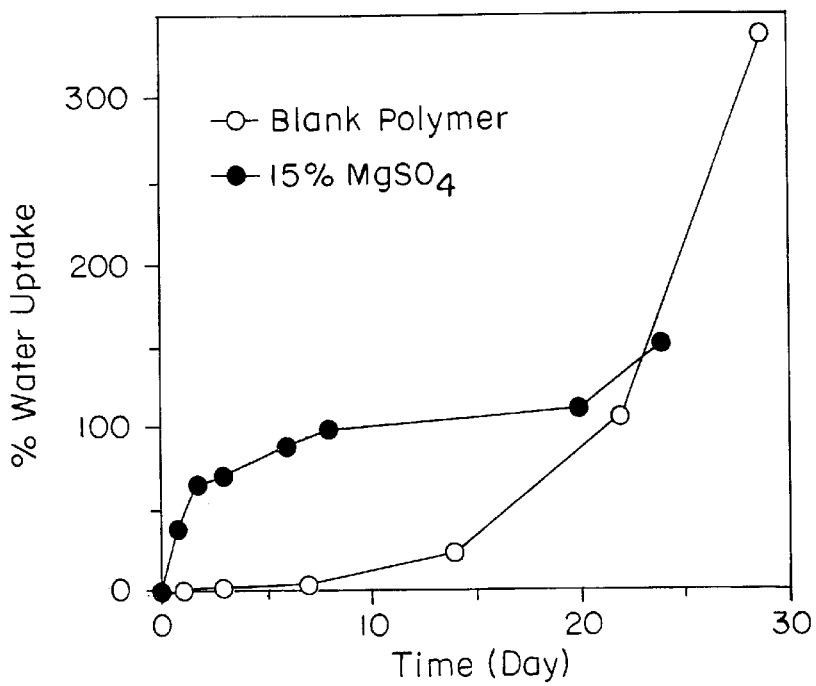
FIG. 7 is a plot of percent water uptake (% w/w) versus hydration time in 10 mM HEPES for the following polymer films: a) blank PLGA and b) PLGA, containing 15% $MgSO_4$, illustrating the effect of $MgSO_4$ on PLGA film water absorption.
Figure 8:
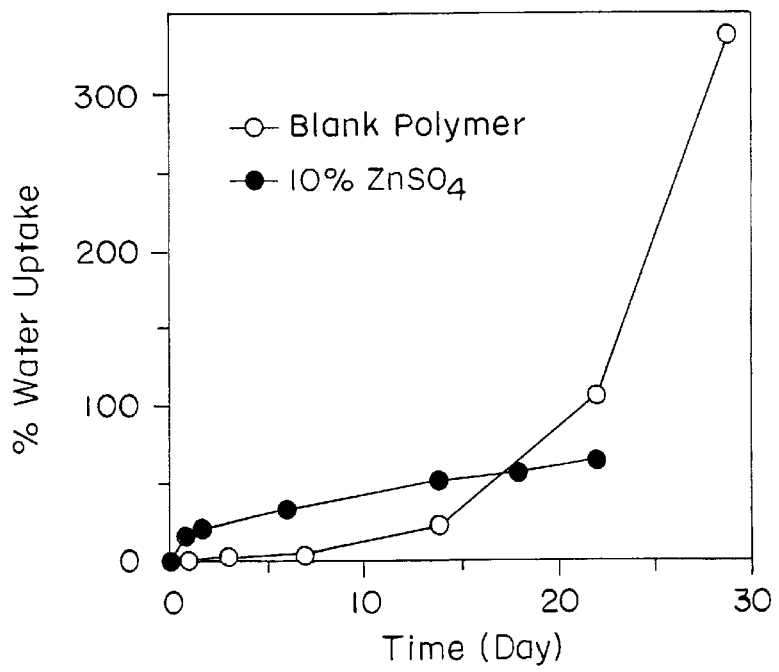
FIG. 8 is a plot of percent water uptake (% w/w) versus hydration time in 10 mM HEPES for the following polymer films: a) blank PLGA and b) PLGA, containing 10% $ZnSO_4$, illustrating the effect of $ZnSO_4$ on PLGA film water absorption.

$Mg(OAc)_2$ containing films showed an initial water uptake that was larger than the blank films (FIG. 5), but not as large as those with the insoluble magnesium salts. No additional water uptake was observed until after 21 days, when a second phase of water uptake took place. The onset of secondary water uptake was delayed by a few days relative to the blank film. Water uptake behavior by $Zn(OAc)_2$, $MgSO_4$ and $ZnSO_4$ films was similar to that of the $Mg(OAc)_2$ film samples (FIGS. 6–8).

Figure 9:
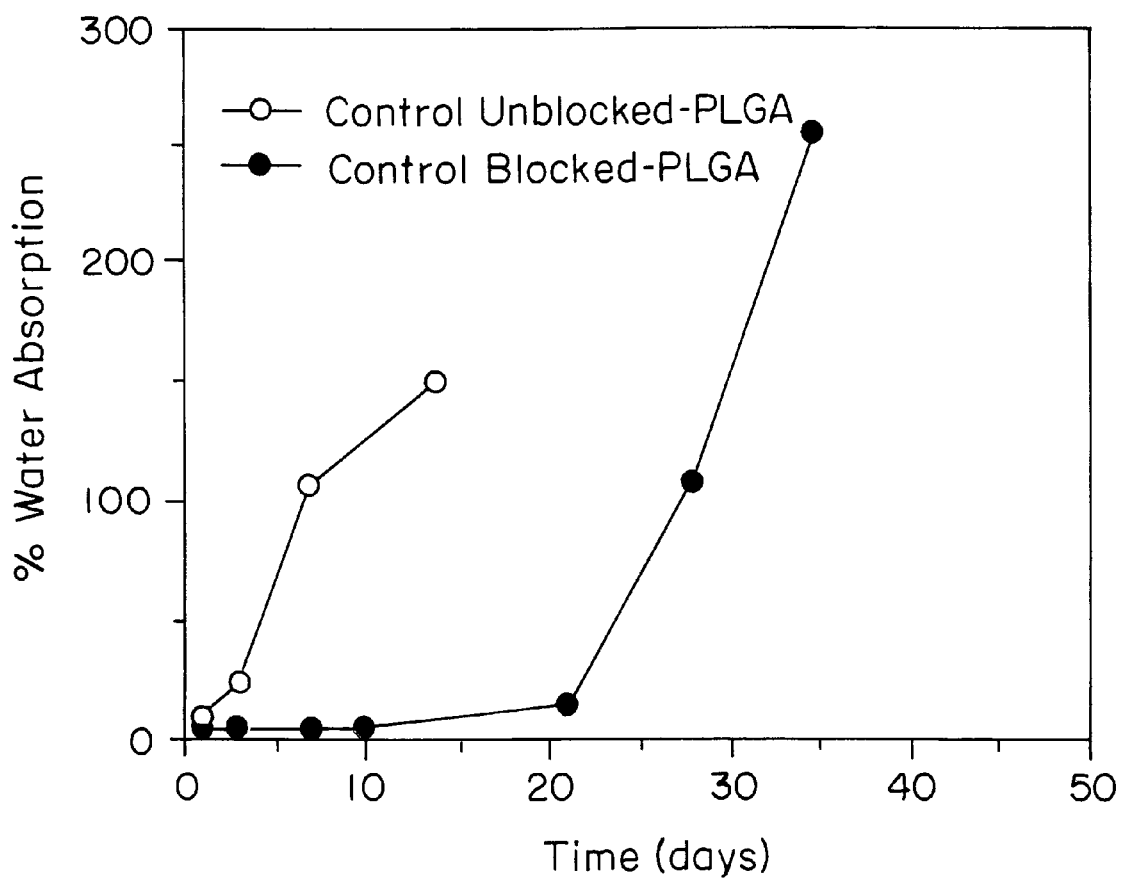
FIG. 9 is a plot of percent water uptake (% w/w) versus hydration time in 10 mM HEPES for the following polymer pellets: a) control blocked-PLGA and b) control unblocked-PLGA, illustrating the effect of PLGA end group characteristics on PLGA pellet water absorption.

The comparative water uptakes of the blocked and unblocked-PLGA pellets are shown in FIG. 9. The initial water uptake over the first 14 days was much greater for the unblocked-PLGA pellet, wherein this pellet absorbed water equal to its dry weight by day 7. By comparison, the blocked-PLGA pellet had only absorbed 3% of its dry weight by day 10. The wet mass of the unblocked polymer could not be determined accurately after day 14 due to the softening and degradation of the polymer pellet.

EXAMPLE IV

EFFECT OF SALTS ON POLYMER DEGRADATION

The effects of encapsulated salts on polymer degradation rates were assessed using molecular weight determined by gel permeation chromatography (GPC). The films of Example I and control pellets of Example II were hydrated as described in Example III. The polymer samples were redissolved in chloroform (5–10 mg/ml) and were filtered through a 0.22 micron filter. GPC was conducted using a MIXED column (300×10 mm, Polymer Labs) with chloroform as eluent and refractive index for detection. Molecular weights were calculated using polystyrene as standards (580 to 950,000 Daltons) and the universal calibration method.

Figure 10:
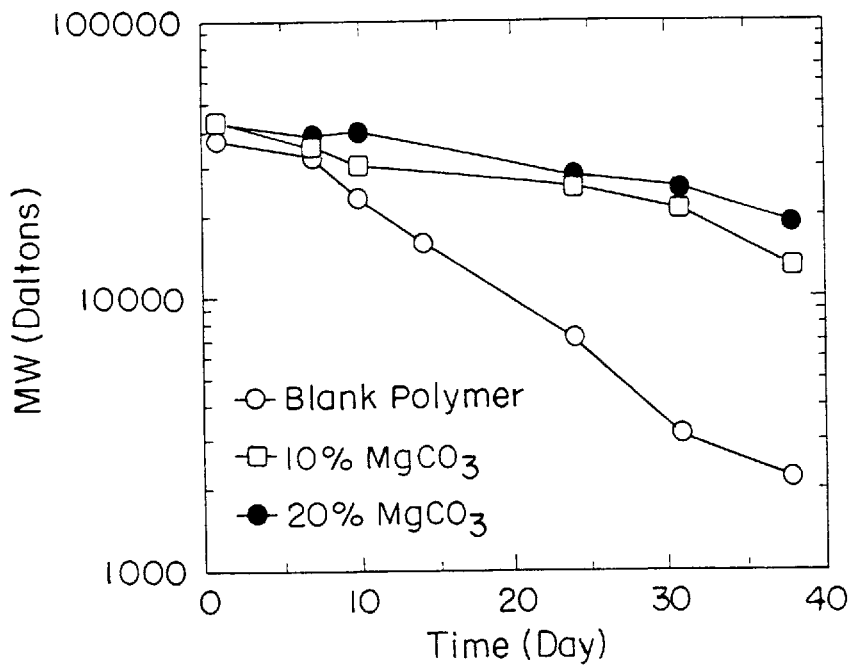
FIG. 10 is a plot of molecular weight as a function of hydration time in 10 mM HEPES for the following polymer films: a) blank PLGA, b) PLGA containing 10% $MgCO_3$, and c) PLGA containing 20% $MgCO_3$, illustrating the effects of $MgCO_3$ at different concentrations on the changes in molecular weight of PLGA films due to hydration.

The molecular weight of the control films decreased from 42000 to 3000 Daltons after 30 days as shown in FIG. 10.

Figure 11:
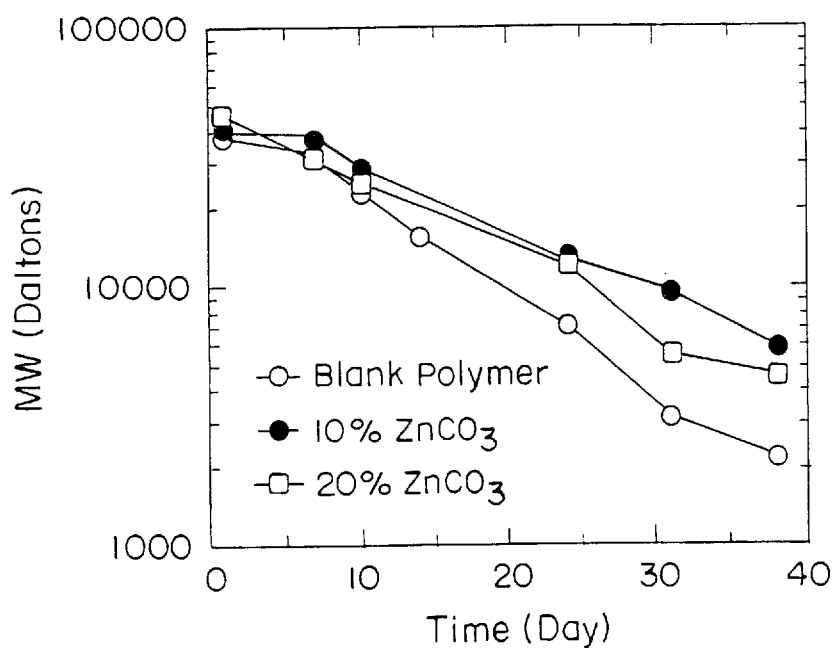
FIG. 11 is a plot of molecular weight as a function of hydration time in 10 mM HEPES for the following polymer films: a) blank PLGA, b) PLGA containing 10% $ZnCO_3$, and c) PLGA containing 20% $ZnCO_3$, illustrating the effects of $ZnCO_3$ at different concentrations on the changes in molecular weight of PLGA films due to hydration.
Figure 12:
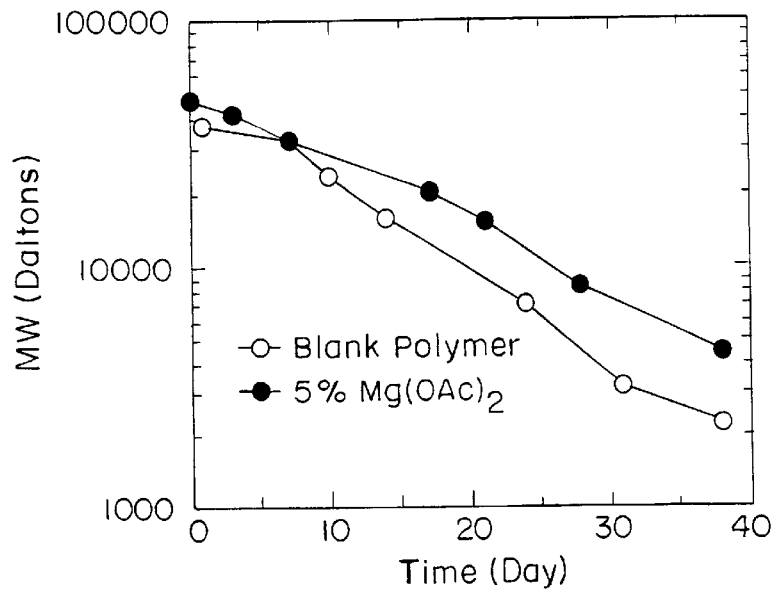
FIG. 12 is a plot of molecular weight (Mw) as a function of hydration time in 10 mM HEPES for the following polymer films: a) blank PLGA and b) PLGA containing 5% Mg(OAc)$_2$, illustrating the effects of Mg(OAc)$_2$ on the molecular weight of PLGA.

In contrast, the rate of decrease in molecular weight of the films containing $MgCO_3$ was smaller than for the control film (see FIG. 10). The molecular weight decrease in films with $ZnCO_3$ was slower than in control films (FIG. 11), but more rapid than in films containing $MgCO_3$. Similar degradation kinetics were observed with $Mg(OAc)_2$ containing films (FIG. 12).

Figure 13:
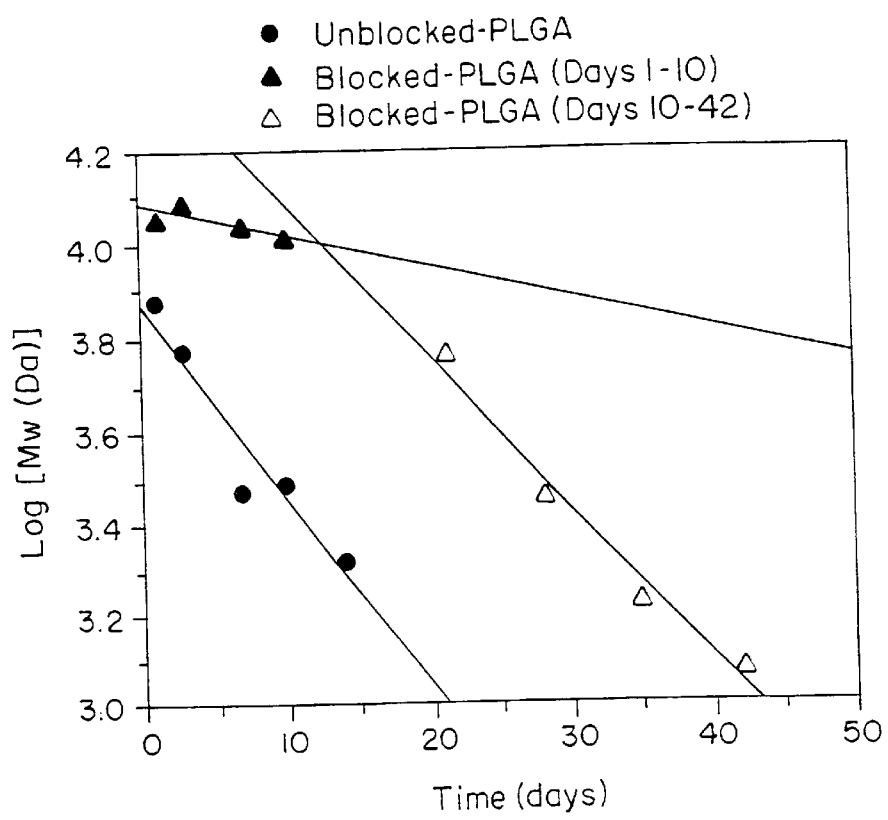
FIG. 13 is a plot of log molecular weight (Mw) as a function of hydration time in 10 mM HEPES for the following polymer pellets: a) unblocked-PLGA and b) blocked-PLGA, illustrating the effects of PLGA end group characteristics on the molecular weight degradation of PLGA due to hydration.

Regarding the control pellets of Example II, shown in FIG. 13, the initial degradation rate of the unblocked-PLGA pellet, as determined by linear least squares fit, was about 6.5 times the initial degradation rate of the blocked-PLGA pellet. After day 10, the degradation rate of the blocked-PLGA pellet became approximately the same as the unblocked-PLGA pellet, which corresponds to the point where water absorption began to increase for the unblocked-PLGA pellet. Thus, for both control pellets, polymer degradation correlated closely with increased water absorption into the control pellets.

EXAMPLE V

EFFECT OF SALTS ON GLASS TRANSITION TEMPERATURE

The glass transition temperature (Tg) of the films was determined using a differential scanning calorimeter (DSC) (DSC 7 Serial, Perkin Elmer, Norwalk, Conn.) under nitrogen and using indium as a standard. Each sample was cooled to 0° C. before heating to 60° C. at 10° C./min. Tg measurements were performed on the film samples after lyophilization as described in Example III.

Figure 14:
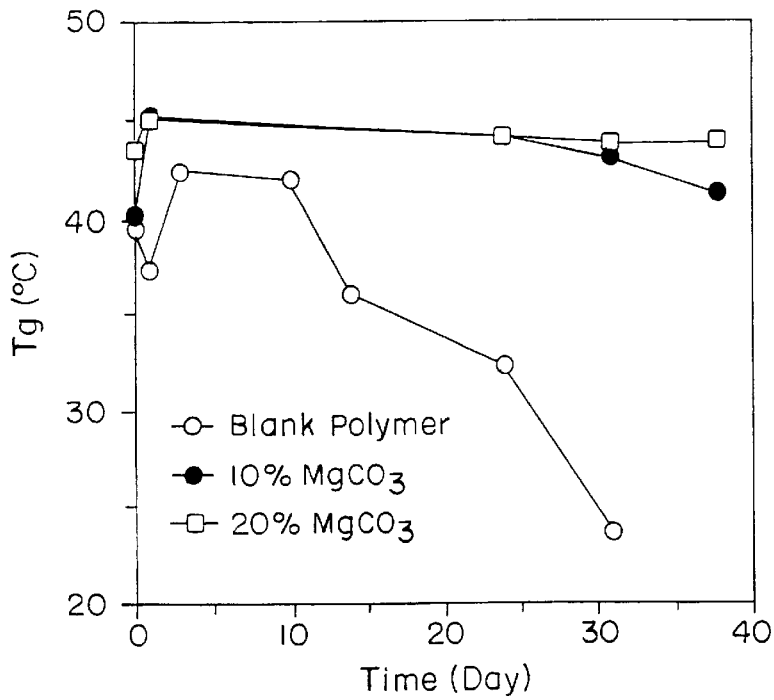
FIG. 14 is a plot of glass transition temperature (Tg) as a function of hydration time in 10 mM HEPES for the following polymer films: a) blank PLGA, b) PLGA containing 10% MgCO$_3$, and c) PLGA containing 20% MgCO$_3$, illustrating the effects of MgCO$_3$ at different concentrations on the changes in the glass transition temperature of PLGA due to hydration.

The time course of Tg decrease for control films is plotted in FIG. 14. The drop in Tg observed between 10 and 15 days corresponds to the point at which the polymer MW decreases to less than 20,000 Daltons.

Figure 15:
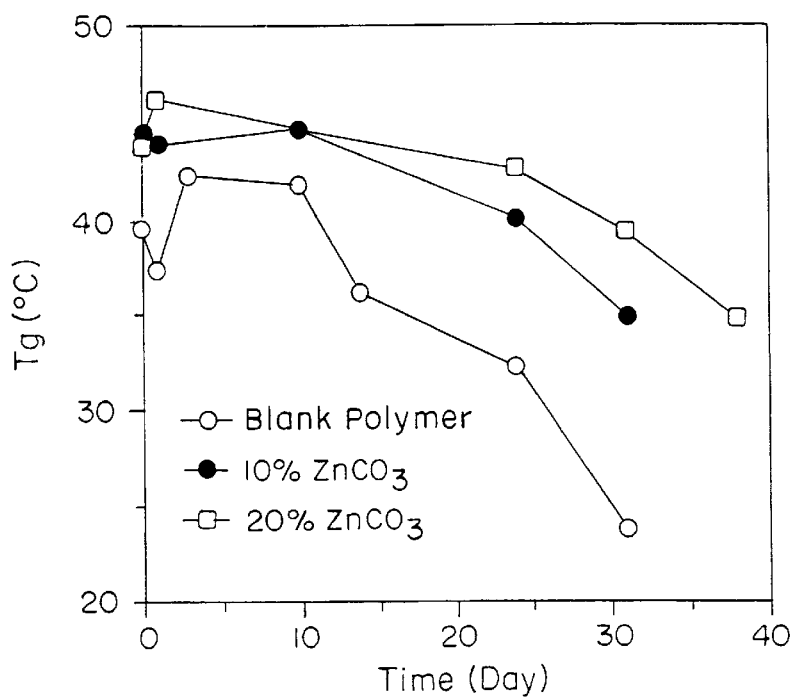
FIG. 15 is a plot of glass transition temperature (Tg) as a function of hydration time in 10 mM HEPES for the following polymer films: a) blank PLGA, b) PLGA containing 10% ZnCO$_3$, and c) PLGA containing 20% ZnCO$_3$, illustrating the effects of ZnCO$_3$ at different concentrations on the changes in the glass transition temperature of PLGA due to hydration.
Figure 16:
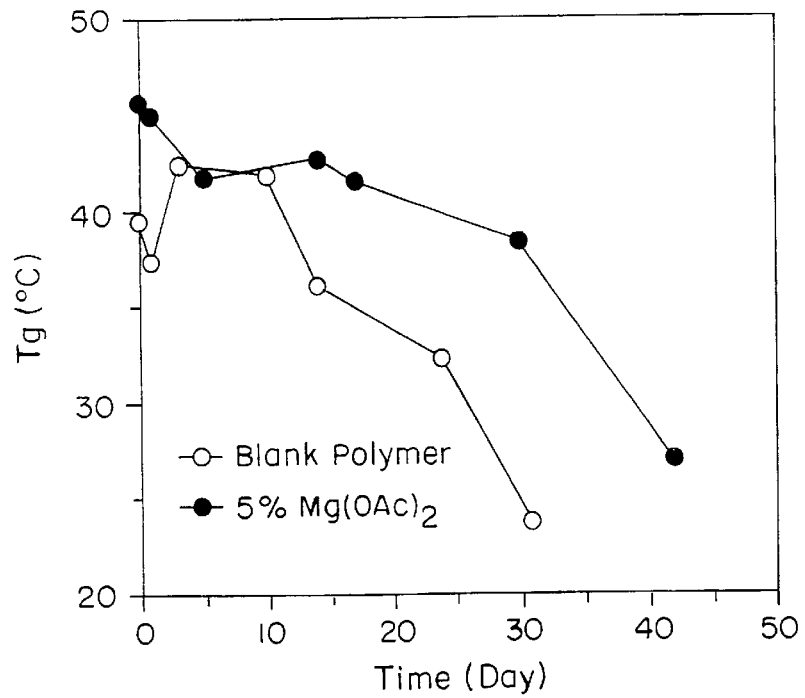
FIG. 16 is a plot of glass transition temperature (Tg) as a function of hydration time in 10 mM HEPES for the following polymer films: a) blank PLGA and b) PLGA containing 5% Mg(OAc)$_2$, illustrating the effects of Mg(OAc)$_2$ on the changes in glass transition temperature of PLGA due to hydration.

In contrast, the rates of Tg decrease in polymer films that contained Mg and Zn salts (FIGS. 14–16) were either negligible (in the case of $MgCO_3$; FIG. 14), or significantly slower ($ZnCO_3$ and $Mg(OAc)_2$; FIGS. 15 and 16, respectively) than those of control films. In $MgCO_3$ and $ZnCO_3$ containing films, a trend toward a slower Tg decrease with increasing salt content was observed.

EXAMPLE VI

EFFECT OF SALTS ON FILM POROSITY

SEM was used to observe qualitative changes in film porosity and to monitor morphology changes of the film surfaces and cross sections over time. Samples were lyophilized as described in Example III. The dried samples were sputter-coated with gold 200–300 Å and the samples observed using JEOL-6400 SEM.

All films displayed a dense structure with a few pores scattered throughout the device prior to hydration. However, the rate of water uptake was different depending on the incorporated salt. Thus the increase in water uptake was not dominated by initial porosity of the sample but was a function of the type of salt dispersed in the polymer film.

SEM evaluation of the control films without salts demonstrated a dense and smooth structure up to 14 days of hydration. Between 14 and 22 days, large pores became visible on the film surface and throughout the sample cross section. The appearance of these pores coincides with the secondary water uptake phase associated with polymer degradation and erosion of the polymer (see Examples III–V).

Films loaded with water insoluble salts exhibited increasing porosity after hydration times as short as 24 hours. SEM analysis of 24 hour hydration samples of films containing 2% $MgCO_3$ showed the formation of a porous network within the film sample, concentrated at the film surface. After 7 days, the film had become uniformly porous across the cross section. Pores ranged in diameter from approximately 1–20 μm. No further increase in porosity was observed between 7 days and 22 days. Similar behavior was observed with films that contained higher $MgCO_3$ percentages.

Films that contained 10% $ZnCO_3$ were also observed to become highly porous within 3 days of hydration. Three day hydration samples showed the presence of a porous network extending throughout the entire film cross section. The morphology of hydrated $ZnCO_3$ containing films was similar to hydrated films with $MgCO_3$.

Films that contained water soluble magnesium salts also exhibited the formation of internal and surface pores and voids well before pore formation occurred in control films. Pores ranging in diameter from approximately 1–50 μm were visible in samples that had been hydrated for 5 days.

There was some difference between the morphology of the films loaded with soluble and insoluble salts that were hydrated for 5 to 7 days. The films loaded with $Mg(OAc)_2$ seemed to display a lower porosity and a tendency toward large voids (approximately 50 microns) compared to films that contained insoluble salts. $MgCO_3$ and $ZnCO_3$ films showed a higher porosity; a majority of the pore volume was composed of pores of less than ten microns in diameter.

EXAMPLE VII

EFFECT OF SALTS ON POLYMER WEIGHT LOSS

The effects of insoluble salts on polymer degradation in hydrated polymer samples were also assessed by monitoring the time course of polymer weight loss during incubation. The films of Example I and the pellets of Example II were hydrated as described in Example III. Samples were recovered at the indicated time intervals and freeze-dried as described in Example III. The weights of the dried polymer samples were gravimetrically measured after lyophilization. Percent weight loss at different times was computed according to the equation:

% Weight Loss $(t)=100 \times (W_{initial}-W_t)/W_{initial}$ where $W_{initial}$ is the initial weight of the polymer and $W_t$ is the weight of the sample at time point t.

Figure 17:
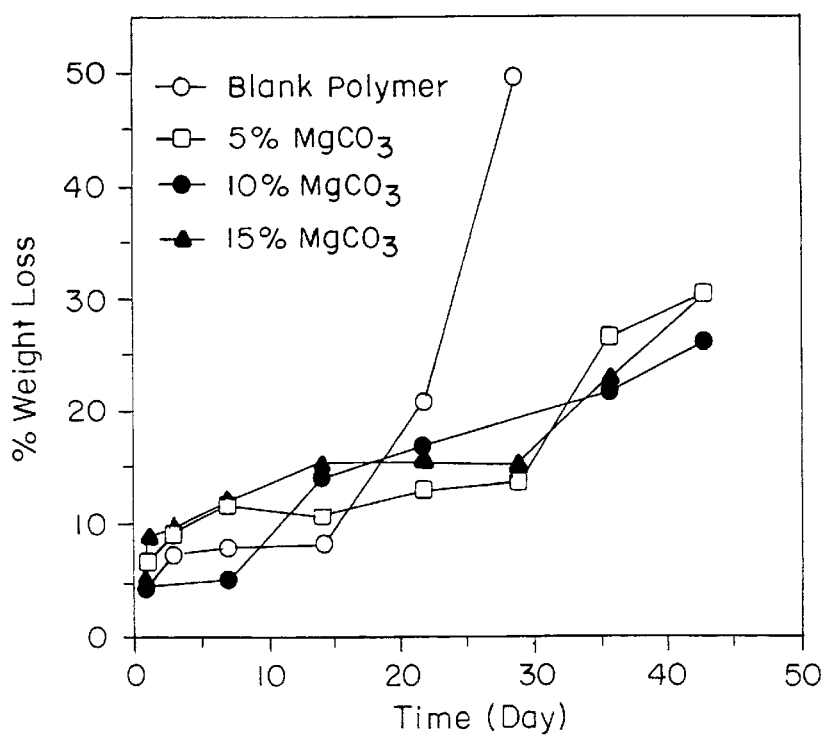
FIG. 17 is a plot of percent weight loss as a function of hydration time in 10 mM HEPES for the following polymer films: a) blank PLGA, b) PLGA containing 5% MgCO$_3$, c) PLGA containing 10% MgCO$_3$, and d) PLGA containing 15% MgCO$_3$, illustrating the effects of MgCO$_3$ at different concentrations on the degradation of PLGA due to hydration.

The effects of different salts on the weight loss of the PLGA films of Example I are shown in FIG. 17. As shown therein, the time course of weight loss in the control film exhibited little weight loss until 14 days, after which rapid weight loss takes place. This phase of weight loss is associated with degradation and erosion of the polymer, as evidenced by increased water uptake, decreased molecular weight and Tg, and the appearance of pores and voids in SEMs of film samples (see Examples III, IV, V, and VI). Also shown in FIG. 17 are weight loss profiles for polymer films that contain 5, 10, and 15% $MgCO_3$. Instead, weight loss in these films was more gradual and of a lesser magnitude.

A portion of the weight loss occurring in $MgCO_3$-containing films was due to dissolution of the encapsulated salt particles. To assess how closely total weight loss measurements approximate polymer weight loss in salt-containing film samples, the polymer weight loss was estimated according to the following two extreme scenarios: (1) all of the encapsulated salt dissolved between the initial hydration and the first time point, and (2) no salt dissolved throughout the entire study. Regardless of which salt dissolution scenario was selected, polymer weight loss in control films exceeded that of $MgCO_3$-containing films, indicating that incorporation of the insoluble salt prevented or delayed is erosion of the polymeric matrix.

Figure 18:
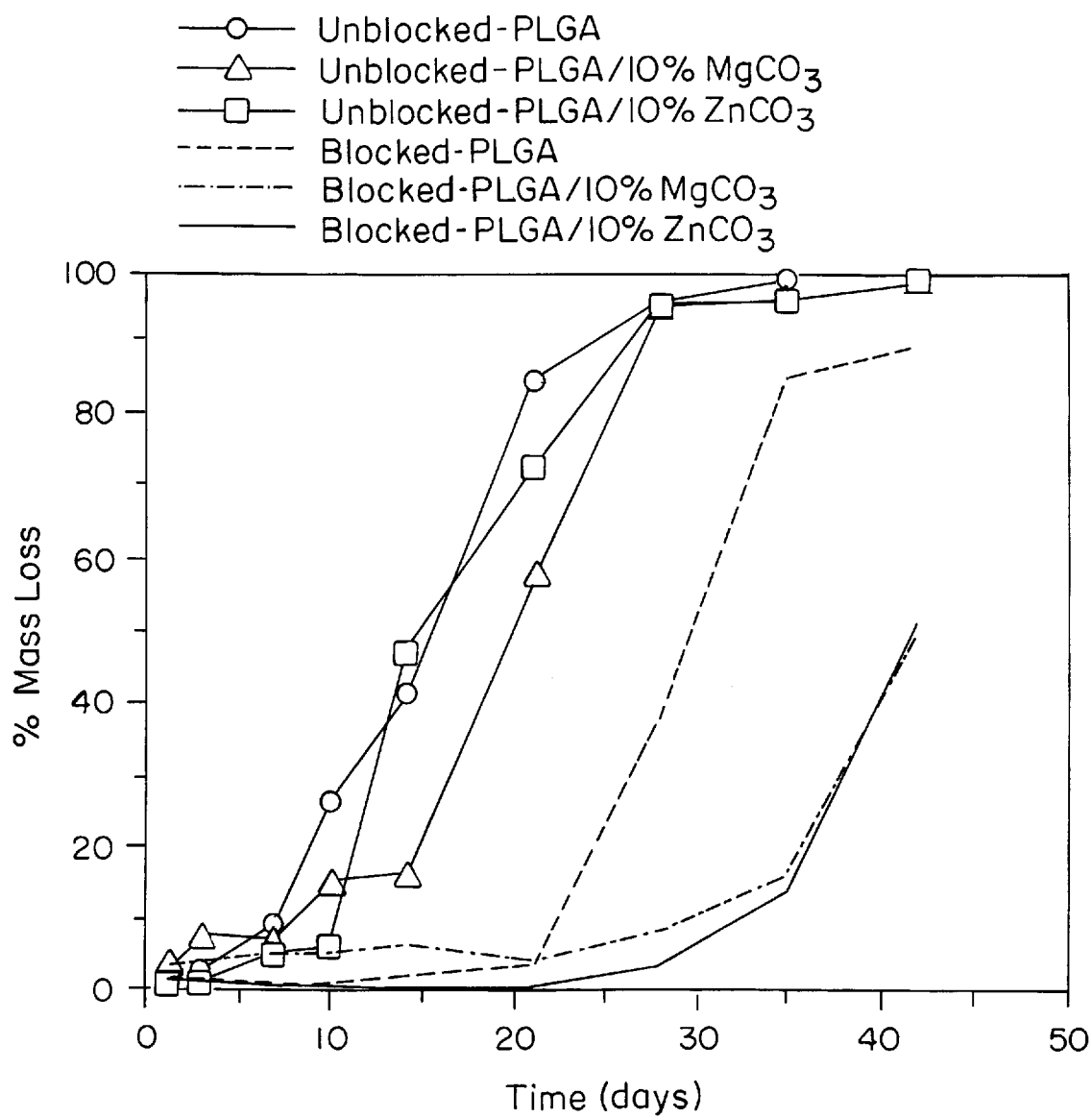
FIG. 18 is a plot of percent mass loss as a function of hydration time in 10 mM HEPES for the following polymer pellets: a) blocked-PLGA, b) unblocked-PLGA, c) blocked-PLGA containing 10% MgCO$_3$, d) blocked-PLGA containing 10% ZnCO$_3$, e) unblocked-PLGA containing 10% MgCO$_3$, and f) unblocked-PLGA containing 10% ZnCO$_3$, illustrating the effects of PLGA end group characteristics and of salts on the degradation of PLGA due to hydration.

The effects of different salts, and of the choice of polymer end group, on polymeric weight loss for the blocked-PLGA and unblocked-PLGA pellets of Example II are shown in FIG. 18. As shown therein, the time course of weight loss in the control blocked-PLGA pellet (blocked-PLGA pellet with 0.0% salt) and the unblocked-PLGA pellet (unblocked-PLGA with 0.0% salt) exhibited little weight loss until day 10 and 20 respectively, after which rapid weight loss takes place. Thus, polymeric degradation can be substantially modulated by choice of the end group of the PLGA.

Also shown in FIG. 18 are weight loss profiles for unblocked-PLGA pellets that contain 10% $MgCO_3$ or 10% $ZnCO_3$. Weight loss in the unblocked-PLGA pellets containing $ZnCO_3$ was not substantially different from the control unblocked-PLGA. Weight loss in the unblocked PLGA pellets containing 10% $MgCO_3$, before day 25, was more gradual.

Further shown in FIG. 18 are weight loss profiles for blocked-PLGA pellets that contain 10% $MgCO_3$ or 10% $ZnCO_3$. Weight loss in the blocked-PLGA pellets containing $MgCO_3$ and $ZnCO_3$ was substantially more gradual and of a lesser magnitude than the control blocked-PLGA pellet. These blocked-PLGA pellets exhibited little weight loss until after day 30.

EXAMPLE VIII

COMPARISON OF THE EFFECT OF ZINC CARBONATE ON IN VIVO AND IN VITRO DEGRADATION OF BLOCKED-PLGA MICROSPHERES

Microspheres of blocked-PLGA (50:50 PLGA, 10,000 Daltons; Lot #115-56-1, Birmingham Polymers, Inc., Birmingham, Ala.), containing 6% w/w $ZnCO_3$, were formed by the method described in U.S. Pat. No. 5,019,400, issued to Gombotz et al. Specifically, the $ZnCO_3$ was added as a particulate to a solution of PLGA in methylene chloride which was sonicated at 4° C. for 30 seconds to form a suspension. The suspension was then sprayed into liquid nitrogen which was overlaying frozen ethanol. The methylene chloride was extracted into the ethanol at −80° C. The microspheres were filtered and lyophilized to produce a dry powder.

The effect of zinc carbonate upon in vitro molecular weight degradation of blocked-PLGA was assessed. The blocked-PLGA microspheres were incubated in HEPES buffer (50 mM HEPES, pH 7.4) in a concentration of 10 mg microspheres/ml at 37° C. Microsphere samples were recovered at the specified time intervals, and freeze dried by freezing at −80° C. and subsequently lyophilized for 2–3 days.

In addition, the effect of zinc carbonate upon in vivo molecular weight degradation of blocked-PLGA was assessed. PLGA microspheres containing 0.0% and 6% w/w ZnCO$_3$ were administered to separate test groups of normal rats (Taconics, Inc.), with three rats in each test group. Microsphere doses of 50 mg were injected, in 750 μl of vehicle (3% carboxymethyl cellulose (low viscosity) and 1% Tween-20 in saline), into the intrascapular region of the rats.

Rats (Sprague-Dawley males) were anesthetized with a halothane and oxygen mixture. The injection sites (intrascapular region) were shaven and marked with a permanent tatoo to provide for the precise excision of skin at the sampling time points. Each rat was injected with an entire vial of microspheres using 18 to 21 gauge needles.

On designated days (days 15 and 30 post-injection) for animals receiving blocked-PLGA microspheres, the rats were sacrificed by asphyxiation with CO$_2$ gas, and the skin at the injection sites (including microspheres) was excised. Remaining microspheres were then collected.

Figure 19:
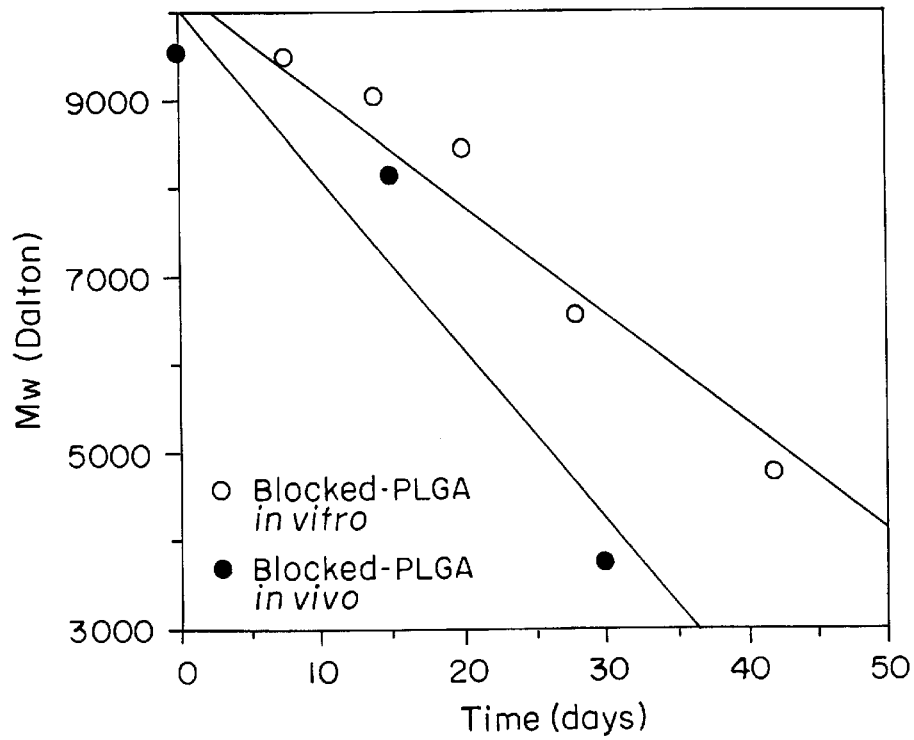
FIG. 19 is a plot of molecular weight (Mw) as a function of time of blocked-PLGA microspheres a) in vitro in 50 mM HEPES and b) in vivo in rats which were subcutaneously administered the microspheres, illustrating the increased degradation rate for in vitro microspheres as compared to in vivo microspheres.
Figure 20:
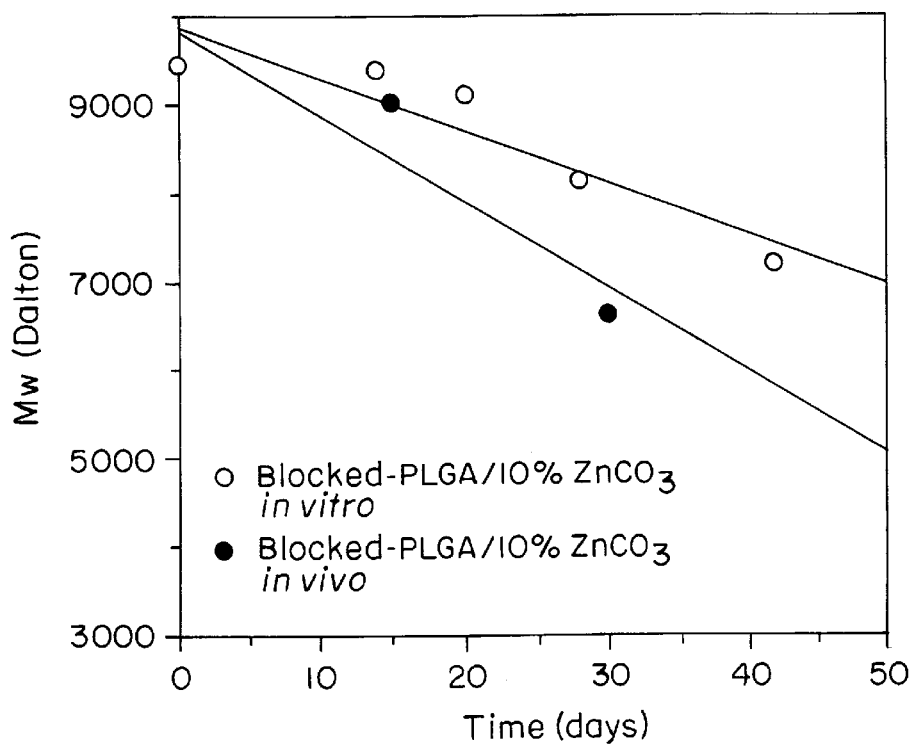
FIG. 20 is a plot of molecular weight (Mw) as a function of time of blocked-PLGA microspheres, containing 10% ZnCO$_3$, a) in vitro in 50 mM HEPES and b) in vivo in rats which were subcutaneously administered the microspheres, illustrating the slower degradation rate of blocked-PLGA microspheres containing 10% ZnCO$_3$ (for in vitro and in vivo), as compared to blocked-PLGA microspheres of FIG. 19, for in vitro microspheres as compared to in vivo microspheres.

The effects of ZnCO$_3$ on the in vitro and in vivo polymer degradation rates of blocked-PLGA polymers were assessed using molecular weight determined by gel permeation chromatography (GPC) as described in Example III. The results of these analyses are provided in FIGS. 19 and 20. As shown therein, the addition of ZnCO$_3$ substantially slowed molecular weight degradation of blocked-PLGA for both in vitro and in vivo microspheres.

EXAMPLE IX

EFFECT OF SALTS ON THE RELEASE OF RNASE-A OR ACTH FROM PLGA MICROSPHERES

A 10 mg/ml RNase-A solution was formed by dissolving RNase-A (R5500; Sigma Chemicals) in deionized water. A buffered adrenocorticotropin hormone (ACTH) was formed by dissolving lyophilized porcine ACTH powder (Diosynth, Chicago, Ill.) in an aqueous 60 mM ammonium bicarbonate buffer.

In separate procedures, each solution (RNase-A solution and buffered ACTH solution) was then micronized using an ultrasonic nozzle (Type V1A; Sonics and Materials, Inc., Danbury, Conn.) and sprayed into liquid nitrogen in a polypropylene tub (17 cm in diameter and 8 cm deep) to form frozen particles of RNase-A solution or frozen particles of buffered ACTH solution. The polypropylene tub was then placed into a −80° C. freezer until the liquid nitrogen evaporated. The frozen RNase-A solution particles or frozen buffered ACTH solution particles were then lyophilized to form lyophilized RNase-A or lyophilized buffered ACTH, respectively.

Lyophilized RNase-A was then microencapsulated into 5000 Dalton blocked-PLGA, (I.V. 0.15 dl/g Birmingham Polymers, Birmingham, Ala.) with either ZnCO$_3$ or Mg(OH)$_2$. The method described in U.S. Pat. No. 5,019,400, issued to Gombotz et al., was used to encapsulate the lyophilized RNase-A (10% w/w) in PLGA containing 0%, 5%, 10% or 15% w/w of salt. Specifically, the lyophilized RNase-A and salt were added as particulates to a solution of PLGA in methylene chloride which was sonicated at 4° C. for 30 seconds to form a suspension. The suspension was then sprayed into liquid nitrogen which was overlaying frozen ethanol. The methylene chloride was extracted into the ethanol at −80° C. The microspheres were filtered and lyophilized to produce a dry powder.

Lyophilized buffered ACTH was also microencapsulated into the same type PLGA with MgCO$_3$ by the method described above.

The effect of the salts upon the in vitro release kinetics of RNase-A and ACTH was assessed. Release studies were conducted by suspending 20 mg of microspheres in 1 ml of 10 mM HEPES buffer at 37° C. Assays were done in 2 ml polypropylene Eppendorf tubes. Release studies of ACTH were conducted in the same manner with the exception of using PBS in lieu of HEPES buffer. At the specified time points, the buffer was removed in full and replaced with fresh buffer. The concentration of RNase-A in buffer was measured using the BCA Protein Assay (Pierce, Rockford, Ill.), and the concentration of ACTH was measured using the Biorad Protein assay (Biorad, Richmond, Calif.).

Figure 21:
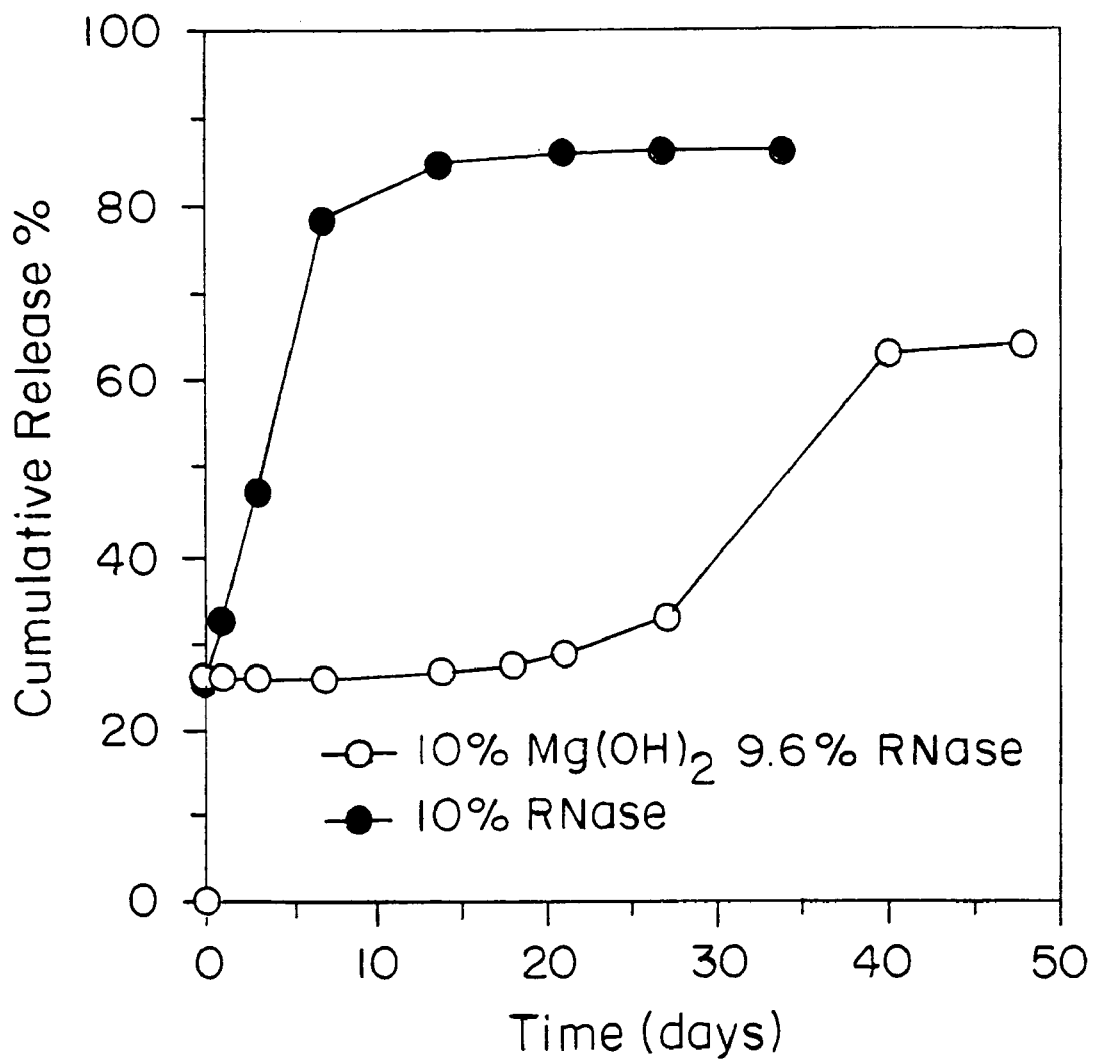
FIG. 21 is a plot of the cumulative percent release of RNase-A in 10 mM HEPES from PLGA microspheres containing 10% RNase-A and either 0% Mg(OH)$_2$ or 10% Mg(OH)$_2$, illustrating the effects Mg(OH)$_2$ on RNase-A release kinetics from PLGA microspheres due to hydration.
Figure 22:
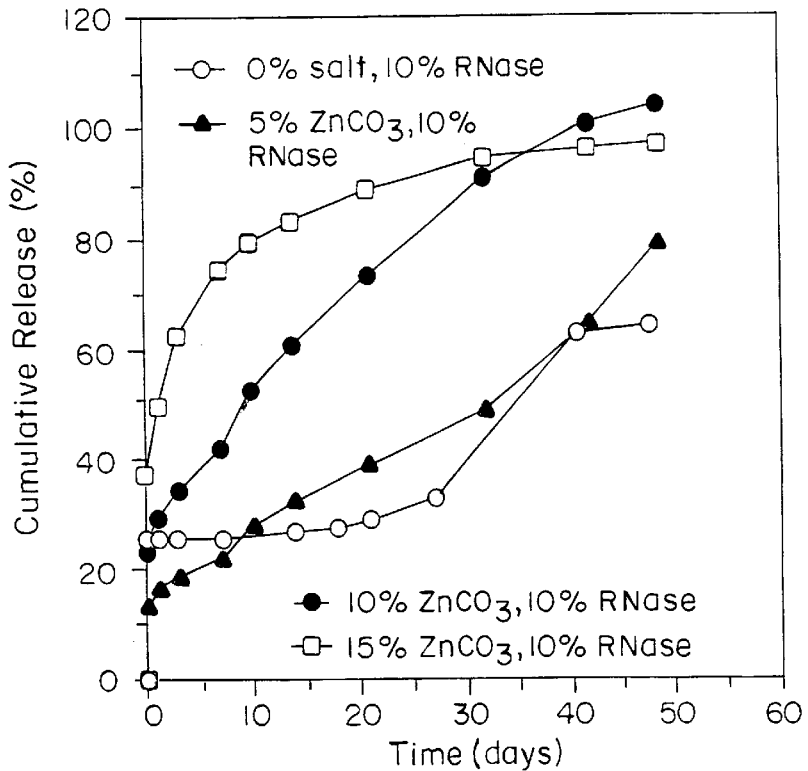
FIG. 22 is a plot of the cumulative percent release of RNase-A in 10 mM HEPES from PLGA microspheres containing 10% RNase-A and either 0% ZnCO$_3$, 5% ZnCO$_3$, 10% ZnCO$_3$, or 15% ZnCO$_3$, illustrating the effects ZnCO$_3$ on RNase-A release kinetics from PLGA microspheres due to hydration.

The effects of Mg(OH)$_2$ or ZnCO$_3$ on the release kinetics of RNase-A are shown in FIGS. 21 and 22. RNase-A encapsulated into PLGA alone exhibited release of the protein over the first 24 hours after which no further release was observed until day twenty one. Mg(OH)$_2$ resulted in continuous release of the protein over 14 days. ZnCO$_3$ resulted in continuous release of the protein over 35 days.

Figure 23:
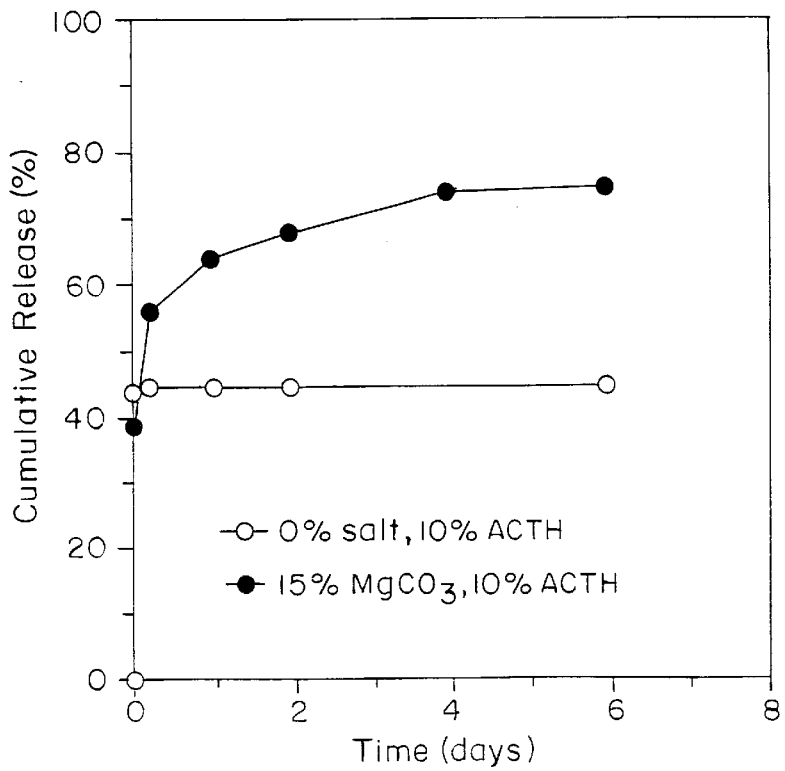
FIG. 23 is a plot of the cumulative percent release of adrenocorticotropin hormone (ACTH) in 50 mM PBS from PLGA microspheres containing 10% ACTH and either 0% MgCO$_3$ or 15% MgCO$_3$, illustrating the effects MgCO$_3$ on ACTH release kinetics from PLGA microspheres due to hydration.

The effect of MgCO$_3$ on the release kinetics of ACTH is shown in FIG. 23. ACTH encapsulated into PLGA alone exhibited approximately 40% release of the protein over the first 24 hours after which no further release was observed. MgCO$_3$ resulted in continuous release of the protein over the same period.

EXAMPLE X

EFFECT OF SALTS ON THE IN VIVO RELEASE OF INTERFERON-A 2,B FROM PLGA MICROSPHERES

The Interferon-α,2b (IFN-α,2b) used herein is identical to the IFN-α,2 described in Rubenstein et al., *Biochem. Biophys. Acta*, 695:705–716 (1982), with the exception that the lysine as position 23 of IFN-α,2 is an arginine in IFN-α,2b. The IFN-α,2b was dissolved in 10 mM sodium bicarbonate buffer (pH 7.2) to form an IFN solution. A 10 mM Zn$^{+2}$ solution was prepared from deionized water and zinc acetate dihydrate, and then was added to the IFN solution, at a molar ratio of 2:1 Zn$^{+2}$:IFN-α,2b to form a solution with a final IFN-α,2b concentration of about 1.3 mg/ml. The pH of the solution was then adjusted to 7.1 by adding 1% acetic acid. A cloudy suspended precipitate, comprising Zn$^{+2}$-stabilized IFN, then formed.

The suspension was micronized, frozen, and lyophilized, as described in Example IX, and then dried to form an IFN powder. Zinc carbonate and IFN powder were added in proportions, by mass, of about 1:1, 3:1 or 8:1 respectively to PLGA solutions containing about 0.4 g PLGA in about 4 ml of methylene chloride, and then were microencapsulated in the PLGA, also as described in Example IX, to form IFN microspheres.

Figure 24:
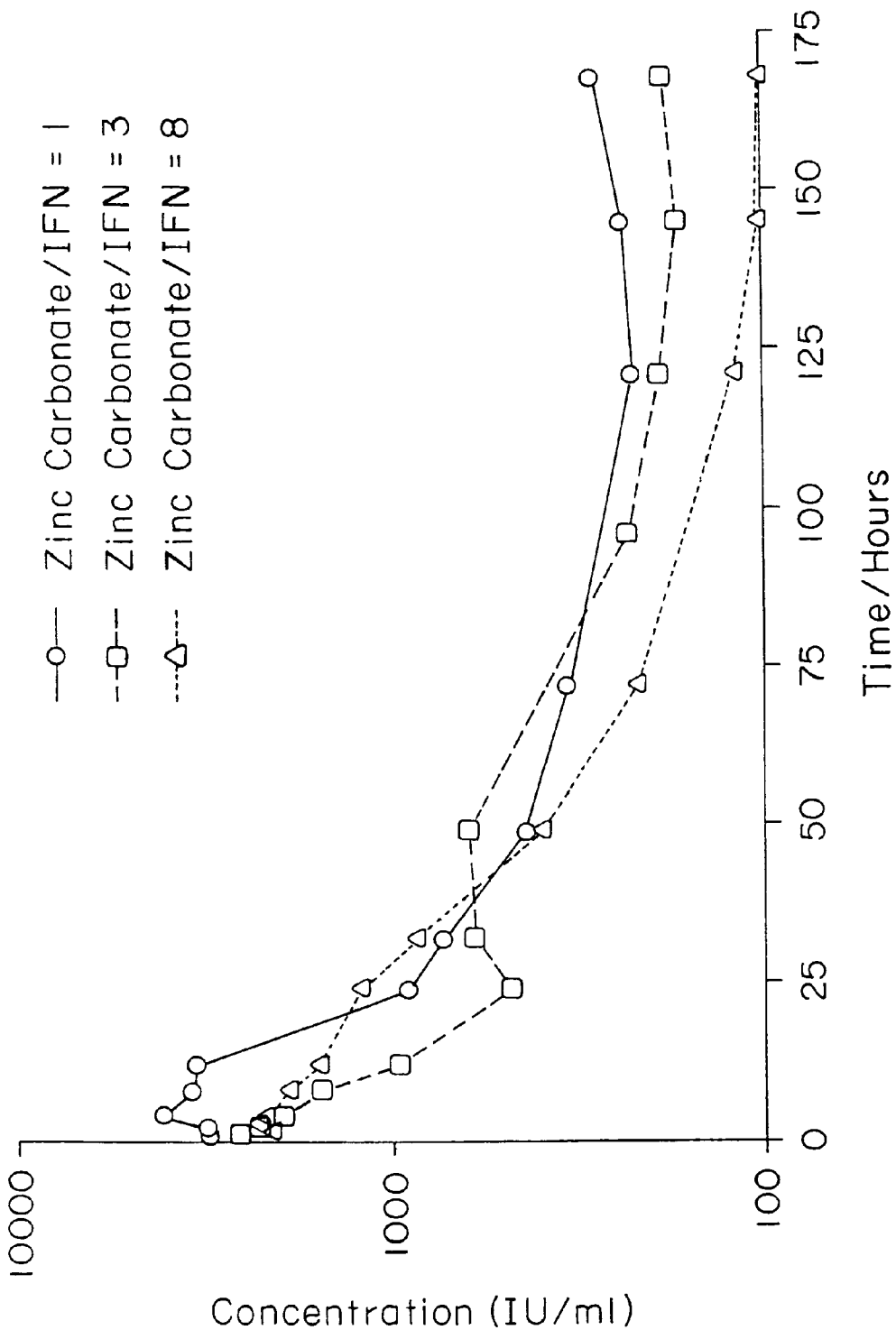
FIG. 24 is a plot of the serum concentration (IU/ml) of Interferon-α,2b in rats which were subcutaneously administered a single injection of microspheres containing zinc carbonate and Zn$^{+2}$-stabilized Interferon-α,2b in molar ratios of a) 1:1, b) 3:1, and c) 8:1 over a seven day period.

The effect of the zinc carbonate upon the in vivo release kinetics of IFN, from lyophilized Zn-IFN precipitate, was then assessed. Each type of IFN microsphere was administered to separate test groups of normal rats (Taconics, Inc.), with three rats in each test group. Microsphere doses of 0.9 mg/kg were injected, in a 0.5% gelatin, 1% glycerol and 0.9% w/w NaCl vehicle, into the intrascapular region of the rats. Blood samples were then taken from the tail vein of each rat at 1, 2, 4, 8, 12, 24, 32, 28, 72, 96, 120, 144, and 168 hours after injection. The IFN-α,2b concentrations in the rat serum samples were then determined using an IFN-α immunoradiometric assay (Celltech, Slough, U.K.). The assay results are presented in FIG. 24, which shows that the sustained release level of immunologically active IFN-α,2b was modulated depending upon the ratio of ZnCO$_3$ to lyophilized Zn-IFN in the PLGA polymer. Higher ratios of ZnCO$_3$:lyophilized Zn-IFN demonstrated lower release rates of IFN-α,2b from the microspheres as measured by IFN-α,2b serum levels.

EXAMPLE XI

EFFECT OF END GROUPS ON IN VIVO PLGA DEGRADATION

Microspheres containing Zn$^{+2}$-stabilized human growth hormone (hGH), whose DNA sequence is described in U.S. Pat. No. 4,898,830, issued to Goeddel et al., were prepared from hydrophilic polymer RG502H having free carboxyl end groups (hereinafter "unblocked-PLGA") (50:50 PLGA, 9,300 Daltons; Boehringer Ingelheim Chemicals, Inc.) or a more hydrophobic polymer having blocked carboxyl end groups (hereinafter "blocked-PLGA") (50:50 PLGA, 10,000 Daltons; Lot #115-56-1, Birmingham Polymers, Inc., Birmingham, Ala.).

The hGH was first Zn$^{+2}$-stabilized by forming an insoluble complex with zinc. A 0.9 mM aqueous solution of zinc acetate was added to a solution of hGH (10 mg/ml) in bicarbonate buffer (0.336 mg/ml) to form an insoluble complex having a Zn:hGH molar ratio of 6:1. The pH of the complex was adjusted to approximately 7.2 with 1% acetic acid.

The method described in Example IX was used to form microspheres by encapsulating 0% or 15% w/w hGH, in the form of Zn:hGH complex, and also 0%, 1% or 6% w/w ZnCO$_3$ salt, within blocked-PLGA and within unblocked-PLGA.

In vivo degradation of unblocked-PLGA microspheres versus blocked-PLGA microspheres was compared by injecting samples of microspheres into rats and then analyzing the microspheres remaining at the injection site at various times post-injection. Three rats were assayed at each time point for each microsphere sample. On the day of administration of the microspheres, 750 µl of vehicle (3% carboxymethyl cellulose (low viscosity) and 1% Tween-20 in saline) was added to vials containing 50±1 mg of microspheres. Immediately, the vials were shaken vigorously to form a suspension which was then aspirated into a 1.0 cc syringe without a needle.

Rats (Sprague-Dawley males) were anesthetized with a halothane and oxygen mixture. The injection sites (intrascapular region) were shaven and marked with a permanent tatoo to provide for the precise excision of skin at the sampling time points. Each rat was injected with an entire vial of microspheres using 18 to 21 gauge needles.

On designated days (days 15, 30, 59, and 90 post-injection for animals receiving blocked-PLGA microspheres, or days 7, 14, 21, 28, and 45 post-injection for animals receiving unblocked-PLGA microspheres) the rats were sacrificed by asphyxiation with CO$_2$ gas, and the skin at the injection sites (including microspheres) was excised. Since the microspheres tended to clump at the injection sites, the presence or absence of microspheres was determined visually.

The visual inspections found that the unblocked-PLGA microspheres degraded substantially faster than the blocked-PLGA microspheres, and that the addition of ZnCO$_3$ to the blocked-PLGA substantially slowed polymeric degradation. For example, in the rats injected with unblocked-PLGA microspheres containing 0% hGH and 0% or 1% ZnCO$_3$, no microspheres were visible on day 21. In addition, for rats injected with blocked-PLGA microspheres containing 0% hGH and 0% ZnCO$_3$, a few microspheres were visible on day 60 and none were visible on day 90. Furthermore, for rats injected with blocked-PLGA microspheres containing 0% or 15% hGH and 6% ZnCO$_3$, microspheres were visible on day 90.

EXAMPLE XII

ASSAY FOR hGH AFTER IN VIVO DEGRADATION OF BLOCKED-PLGA Zn$^{+2}$-STABILIZED hGH MICROSPHERES

Microspheres of blocked-PLGA, containing 16% w/v Zn$^{+2}$-stabilized hGH and 0%, 6%, 10% or 20% ZnCO$_3$ were formed by the method of Example IX. Groups of test rats were injected with 50 mg samples of the different hGH microspheres, also as described in Example XI. The rats were sacrificed after 60 days, and the skin sample were excised from the injection sites. The excised skin samples were placed in 10% Neutral Buffered Formalin for at least 24 hours. They were then trimmed with a razor blade to remove excess skin and placed in PBS. Tissue samples were processed by Pathology Associates, Inc. (Frederick, Md.). The skin samples were embedded in glycomethacrylate, sectioned and assayed for the presence of hGH using a HistoScan/LymphoScan Staining Kit (Product #24–408 M; Accurate Chemical & Scientific Corp., Westbury, N.Y.) according to the manufacturer's instructions. Tissue samples were scored for the presence or absence of staining which was indicative of the presence or absence of hGH in the sample. All skin samples, associated with hGH microsphere injections, tested positive for the presence of hGH, thus indicating that the blocked-PLGA microspheres still contained hGH after 60 days in vivo.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of delivering a biologically active agent to an individual in need thereof comprising the step of administering to said patient a composition for the modulated release of a biologically active agent comprising:
    a) a biocompatible polymer matrix;
    b) an effective amount of a biologically active agent, wherein the biologically active agent is dispersed within the polymer matrix; and
    c) one or more metal cation components for modulating release of the biologically active agent from the polymer matrix wherein the metal cation component comprises a cation selected from the group consisting of Zn(II), Mg(II) and a combination of at least two different multivalent metal cations, and wherein the metal cation component is separately dispersed within the polymer matrix.

2. The method of claim 1 wherein said metal cation component is selected from the group consisting of magnesium hydroxide, magnesium carbonate, zinc carbonate, magnesium acetate, zinc acetate, magnesium chloride, zinc chloride, magnesium sulfate, zinc sulfate, magnesium citrate and zinc citrate.

3. The method of claim 1 wherein said polymer is a biodegradable polymer.

4. The method of claim 3 wherein said biodegradable polymer is selected from the group consisting of poly (lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polycaprolactone, polyesteramides, blends and copolymers thereof.

5. The method of claim 1 wherein said biologically active agent is a protein selected from the group consisting of nucleases, erythropoietin, human growth hormone, interferons, interleukins, growth factors, tumor necrosis factor, adrenocorticotropic hormone, and colony-stimulating factors.

6. A method of delivering a biologically active agent to an individual in need thereof comprising the step of administering to said patient a composition for the modulated release of a biologically active agent comprising:
   a) a biocompatible polymer matrix of a poly(lactide-co-glycolide) polymer;
   b) an effective amount of a biologically active agent, wherein said biologically active agent is dispersed within the polymer matrix; and
   c) one or more metal cation components for modulating release of the biologically active agent from the polymer matrix, wherein the metal cation component comprises a cation selected from the group consisting of Zn(II), Mg(II) and a combination of at least two different multivalent metal cations and wherein the metal cation component is separately dispersed within the polymer matrix.

7. The method of claim 6 wherein said metal cation component is selected from the group consisting of magnesium hydroxide, magnesium carbonate, zinc carbonate, magnesium acetate, zinc acetate, magnesium sulfate, zinc sulfate, magnesium chloride, zinc chloride, zinc citrate, magnesium citrate and a combination thereof.

8. The method of claim 6 wherein said biologically active agent is a protein selected from the group consisting of nucleases, erythropoietin, human growth hormone, interferons, interleukins, growth factors, tumor necrosis factor, adrenocorticotropic hormone and colony-stimulating factors.

* * * * *